United States Patent [19]

Curtiss et al.

[11] Patent Number: 4,677,057
[45] Date of Patent: Jun. 30, 1987

[54] DIAGNOSTIC ASSAY FOR THE PRESENCE OF APOLIPOPROTEINS ASSOCIATED WITH PLASMA HIGH DENSITY LIPOPROTEINS

[75] Inventors: Linda K. Curtiss, San Diego; Thomas S. Edgington, La Jolla, both of Calif.

[73] Assignee: Scripps Clinic and Research Foundation, La Jolla, Calif.

[21] Appl. No.: 710,038

[22] Filed: Mar. 11, 1985

[51] Int. Cl.$^4$ .................. G01N 33/53; G01N 33/543; C12N 15/00; C12N 5/00
[52] U.S. Cl. .................................. 435/7; 435/172.2; 435/240; 435/241; 435/948; 436/518; 436/533; 436/540; 436/548; 436/808; 436/809; 436/811; 935/89; 935/95; 935/110; 530/359; 530/387; 530/388; 530/808; 530/809
[58] Field of Search ................ 260/112 B, 112 R; 435/948, 172.2, 240, 211, 7; 935/89, 93, 95, 103, 106, 108, 110; 436/548, 518, 533, 538, 539, 540, 544, 545, 808, 809, 811; 530/359, 387, 388, 808, 809

[56] References Cited

U.S. PATENT DOCUMENTS 4,399,217 8/1983 Halmquist et al. .................. 435/7

OTHER PUBLICATIONS

Köhler and Milstein, Nature, vol. 256, pp. 495-497 (1975).
El Morshidy, Dissertation Abstracts International B, vol. 45, No. 3, p. 821, 1984.
Steinberg et al., Clin. Chem., vol. 29, No. 3, pp. 415-426, 1983.
Ventrex Laboratories Inc. Catologue, RIA for Apolipoprotein A-1, 1984.

Primary Examiner—Sidney Marantz
Assistant Examiner—Patricia L. DeSantis
Attorney, Agent, or Firm—Dressler, Goldsmith, Shore, Sutker & Milnamow Ltd.

[57] ABSTRACT

Monoclonal receptors that immunologically bind to human apolipoprotein A molecules, particularly apo-A-I and apo-A-II, are described as are their methods of use and articles of manufacture containing them.

33 Claims, 10 Drawing Figures

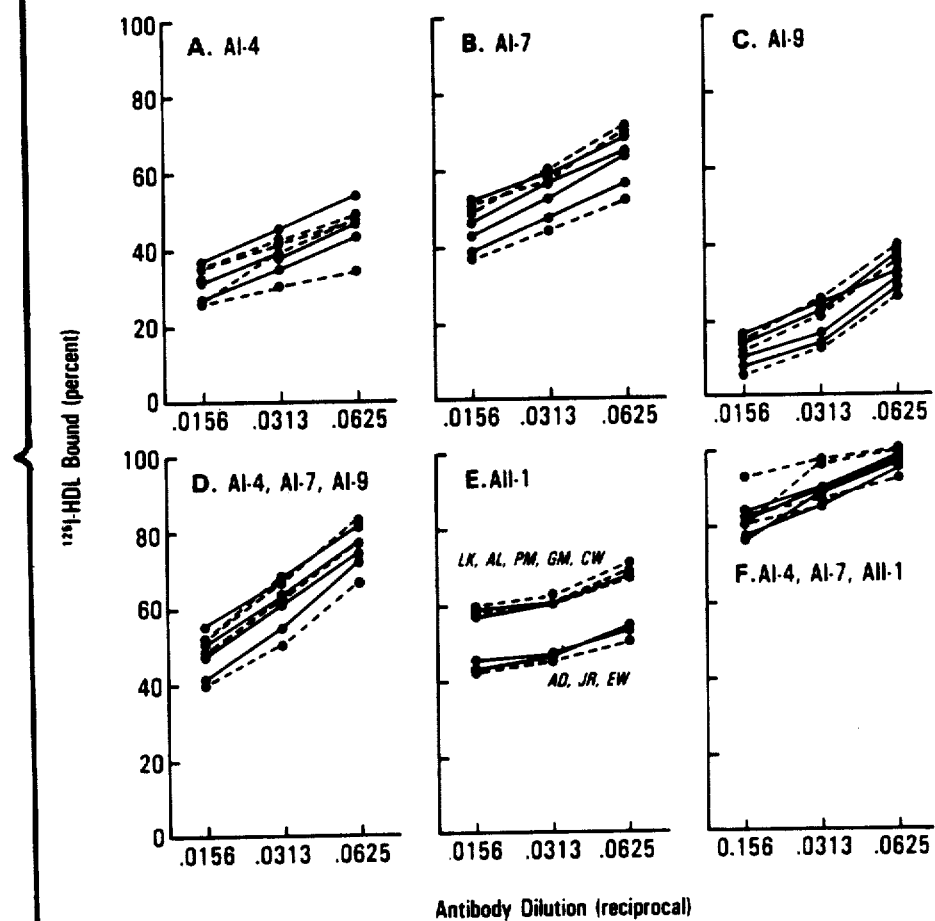

DIAGNOSTIC ASSAY FOR THE PRESENCE OF APOLIPOPROTEINS ASSOCIATED WITH PLASMA HIGH DENSITY LIPOPROTEINS

DESCRIPTION

1. Technical Field of the Invention

The present invention relates to epitope-specific reagents that bind apolipoproteins, and particularly to monoclonal receptors that form immunoreactants with apolipoprotein A thereby permitting a determination of the immunochemical heterogencity of lipoproteins.

Background of the Invention

A. Atherosclerosis and Lipoproteins

Atherosclerosis is the disease in which cholesterol and other lipids, accumulating on the walls of arteries, form bulky plaques that inhibit the flow of blood and may lead to the formation of a clot, obstructing an artery and causing occlusive thrombotic or embolic disease such as a heart attack or stroke. Up to 50 percent of all deaths in the United States are caused by atherosclerosis and its secondary complications.

Human atherosclerosis is defined as the accumulation of selected lipids, including cholesterol, and cells in the walls of arteries and with time produces occlusive lesions. Although the etiology of atherosclerosis is multifactorial, a large body of clinical, pathologic, genetic and experimental evidence suggests that abnormalities of lipoprotein metabolism can contribute to the development of atherosclerosis. These lipids are carried in the blood stream as lipid-protein complexes called lipoproteins.

Atherosclerosis, and particularly that form known as coronary artery disease (CAD), is a major health problem. Atherosclerosis and its related vascular diseases acounted for 983,000 deaths in 1983; and CAD alone accounts for more deaths annually than all forms of cancer combined. In the United States, more than 1 million heart attacks occur each year and more than five hundred thousand people die as a result of this disease. In direct health care costs, CAD costs the United States more than $60 billion a year. This enormous toll has focused attention on ways to identify particular populations at risk for CAD so that the disease can be controlled with diet, behavioral modification (exercise); and specific therapeutic agents.

Four major classes of cholesterol-associated plasma lipoprotein particles have been defined, and have their origin in the intestine or liver. These particles are involved in the transport of the neutral lipids including cholesterol and triglycerides. All classes of plasma lipoproteins have apolipoproteins associated with the lipid-protein complex; and the apolipoproteins play requisite roles in the function of these lipoproteins.

The first class is the chylomicrons. They are the largest of the lipoproteins and are rich in triglycerides. The site of origin of the chylomicrons is the intestine.

While apolipoproteins are a quantitatively minor proportion of the mass of chylomicrons, apolipoproteins A-I, A-II and A-IV are significantly associated with chylomicrons, and intestinal synthesis of these A apolipoproteins has been found. Much of the chylomicron complement of A apolipoproteins is lost, and C and E apolipoproteins are acquired when chylomicrons are exposed to plasma or HDL in vitro. Intestinal production of the A apolipoproteins (apo-A) may be regulated by factors other than fat absorption and chylomicron formation.

The next class of lipoproteins is the very low density lipoproteins, VLDL. The VLDL particle is involved in triglyceride metabolism and transport of these lipids from the liver. The apolipoproteins, apo-B and apo-E are the major constituents of the VLDL particle.

The third lipoprotein is called low density lipoprotein (LDL), and is a specific product of the catabolism of VLDL. The predominant apolipoprotein in the LDL particle is apolipoprotein B, or apo-B. Analytical techiques have revealed that apo-B is also the specific apolipoprotein associated with chylomicrons and VLDL.

The results of the now classic Framingham study (1971) showed a clear correlation between risk for CAD and serum cholesterol levels. This study also demonstrated that elevated levels of low density lipoprotein (LDL) cholesterol are associated with increased risk of CAD. Recently, a study conducted by the Lipid Research Clinics Coronary Primary Prevention Trial (1984) has demonstrated that plasma levels of cholesterol and LDL cholesterol can be reduced by a combined regime of diet and drugs, and that this reduction of plasma cholesterol results in reduction of the incidence of CAD mortality.

The cholesterol of atherosclerosis plaques is derived in part, if not mostly from low-density lipoprotein (LDL). LDL is a large spherical particle whose oily core is composed of about 1500 molecules of cholesterol, each attached by an ester linkage to a long chain fatty acid. This core of cholesterol is enclosed by a layer of phospholipid and unesterified cholesterol molecules. The phospholipids are arrayed so that the hydrophilic heads are on the outside, allowing the LDL to be in hydrated suspension in the blood or extracellular fluids.

The cholesterol delivered to, and liberated from LDL particles taken up by cells, controls cell's cholesterol metabolism. An accumulation of intracellular cholesterol modulates three processes.

First, it reduces the cell's ability to make its own cholesterol by turning off the synthesis of an enzyme, HMG CoA reductase, that catalyzes a step in cholesterol's biosynthetic pathway. Suppression of the enzyme leaves the cell dependent on external cholesterol derived from the receptor-mediated uptake of LDL.

Second, the incoming LDL-derived cholesterol promotes the storage of cholesterol in the cell by activating an enzyme denominated lipoprotein acyltransferase. That enzyme esterifies fatty acids to excess cholesterol molecules, making cholesteryl esters that are deposited in storage droplets.

Third, and most significant, the accumulation of cholesterol within the cell drives a feedback mechanism that makes the cell stop synthesizing new LDL receptors. Cells thereby adjust their complement of external receptors so that enough cholesterol is brought into the cells to meet the cells' varying demands but not enough to overload them. For example, fibroblasts that are actively dividing, so that new membrane material is needed, maintain a maximum complement of LDL receptors of about 40,000 per cell. In cells that are not growing, the incoming cholesterol begins to accumulate, the feedback system reduces receptor manufacture and the complement of receptors is reduced as much as tenfold.

On the other hand, it has been shown that another circulating lipoprotein, high density lipoprotein (HDL)

is implicated in a state of elevated cholesterol associated with lowered risk of atherosclerosis. Apolipoprotein A is a ligand of the HDL particle. The amount of HDL provides an inverse correlation with the predicted incidence of atherosclerosis.

High density lipoprotein (HDL) contains two major apolipoproteins, apo-A-I and apo-A-II. Apo-A-I is the major protein component of all primate HDL. All HDL particles contain apo-A-I, and therefore immuno quantification of HDL has usually involved the quantitation of apo-A-I. HDL particles containing only apo-A-II have not been described.

One function of apo-A-I is the activation of the plasma enzyme, lecithin-cholesterol acyltransferase (LCAT). This enzyme is required for the esterification of free cholesterol for transport to the liver. In the absence of apo-A-I, cholesterol in the blood is not esterified and thus cholesterol is not cleared from the blood. The specific role in HDL metabolism served by apo-A-II has not been defined.

Many studies have shown that elevated HDL levels correlate with a reduced incidence of CAD. Some authors have speculated that HDL removes cholesterol from peripheral sites, such as the arterial wall, therefore attributing anti-atherogenic properties to HDL. Higher concentrations of HDL cholesterol are correlated with a lower incidence of and/or a decreased severity of cardiovascular disease, while elevated levels of LDL cholesterol are associated with an increased risk of CAD. For the proper management of patients with hyperlipidemia (excess lipids in the blood) and those patients at special risk for CAD, it is desirable to frequently determine levels of LDL and HDL cholesterol.

To date, assays of HDL cholesterol have been cumbersome and inaccurate in determining blood levels of HDL. It would therefore be beneficial to provide an assay that is easy to use and accurately determines HDL blood levels.

B. Lipoprotein Structure and Function

It is important to understand that cholesterol does not exist free in plasma but is transported to tissue sites in the body by lipoproteins. Cholesterol can be obtained from directed cellular synthesis or by diet. However, cholesterol can be removed from the host only by the liver, where it is converted to bile acids and excreted.

Very low density lipoprotein (VLDL) carries cholesterol and triglycerides to the liver for subsequent excretion, whereas, LDL delivers cholesterol to extrahepatic tissues, including the coronary arteries. Hence, the "bad" lipoprotein, LDL/apo-B, is involved in the deposition of cholesterol in peripheral tissue. Conversely, the "good" lipoprotein HDL/apo-A, removes cholesterol from the tissues and returns cholesterol to the liver for excretion.

Historically, many systems have been developed to isolate and to characterize lipoproteins. These techniques are usually based upon the physicochemical properties of the lipoprotein particles. The two most frequently used techniques are ultracentrifugation and electrophoresis.

Differential density gradient ultracentrifugation takes advantage of the fact that the lipoproteins are lighter or less dense, than other plasma proteins, and it is easy to separate the chylomicrons (the lightest lipoproteins), VLDL, LDL and HDL from each other. Electrophoretic techniques have been useful for the classification of patients with hyperlipidemias. However, these techniques are not easily carried out in an ordinary clinical laboratory.

One can also see that the simple quantitation of blood cholesterol or triglycerides does not provide the physician with the specific information about which lipoproteins are carrying these lipids and their quantitation.

C. The Plasma Lipoproteins

Four major classes of plasma lipoproteins; i.e., chylomicrons, VLDL, LRL and HDL, have been defined, and subclasses within these undoubtedly exist. All lipoproteins have their origin in the intestine or liver, or both, and appear to have a pseudomicellar structure. Neutral lipids, and particularly, cholesterol esters and triglycerides, are maintained in the lipoproteins in a soluble and stable form through interactions with the apolipoproteins and phospholipids, which are more polar.

Unesterified cholesterol is also present in these complexes. Its polarity lies between that of the neutral lipids (cholesteryl esters and triglycerides) and that of the more polar apolipoproteins and phospholipids.

An outer surface consisting of apolipoproteins, unesterified cholesterol, and phospholipids surrounds a water-insoluble core of cholesteryl esters and triglycerides, protecting the apolar lipids from the aqueous environment. This general structural concept has been supported by low-angle x-ray scattering studies and by other physical methods in which a variety of probes have been used to explore the structure of the lipoproteins. An important function of the plasma lipoproteins is thus the solubilization and transport of the neutral plasma lipids.

D. The Apolipoproteins

Apolipoproteins are the lipid-free protein components of the plasma lipoproteins obtained by treating intact lipoproteins with organic solvents, detergents, or chaotropic agents. Not all proteins captured with lipoproteins necessarily have a role in lipid transport. A pertinent example is the recent recognition that the serum amyloid A proteins, acute phase reactants, are transported in plasma bound to HDL. These low molecular weight proteins may comprise up to 30 percent of apo-HDL in inflammatory states, but it is doubtful that they have specific lipid transport roles.

1. Apolipoproteins A-I and A-II

Two of the apolipoproteins of interest in the present invention are apolipoprotein A-I (apo-A-I) and apolipoprotein A-II (apo-A-II). These are discussed below.

Apo-A-I is the major protein component of all primate HDL. It consists of a single chain of 243 to 245 residues; does not contain cystine, cysteine, leucine, or carbohydrate; and exists in several isoforms. Apo-A-I has an alpha helical content of about 55 percent in the lipid-free state, which increases to about 75 percent upon binding phospholipid. Repeating cycles of 11 helical residues have been identified in this apolipoprotein. It has been suggested that these units represent a single ancestral chain which, by gene duplication, has generated a 22-residue repeat unit. These units have close sequence homology and are believed to represent the lipid-binding regions of the protein.

Apo-A-I is potent activator of LCAT, a plasma enzyme that catalyzes the conversion of cholesterol and phosphatidylcholine to cholesteryl ester and lysophosphatidylcholine, respectively. Specific lipid-binding regions of apo-A-I have been found to activate LCAT, and this activity has been associated with the property of lipid binding. As already noted, liver and intestine synthesize apo-A-I, but their relative contributions to the total plasma content and the factors modulating apo-A-I production are not well defined. Typically, more than about 90 percent of plasma apo-A-I is associated with HDL, less than about 1 percent with VLDL and LDL, and about 10 percent or less is associated with the lipoprotein-free fraction of plasma.

Apo-A-II is also a major constituent of human HDL, accounting for about one-third of the total protein and about 15 percent of HDL mass. It exists as a dimer of two identical chains of 77 residues, which are linked covalently at the cysteine of position 6 from the amino-terminus by a disulfide bond, and its primary structure is known. Both the monomeric and dimeric forms of apo-A-II are capable of reassembling with phospholipid. The alpha helix content of apo-A-II increases from about 40 to 65 percent on interaction with egg lecithin, and specific lipid binding segments have been identified and synthesized.

The specific role of apo-A-II in lipid transport has not been identified, and it is a quantitatively minor HDL apolipoprotein in most lower species. The bulk of plasma apo-A-II is found in HDL, with less than about 5 percent in other density classes.

2. Clinical Importance of Apo-A Lipoproteins

Measurement of the major protein constituent of HDL, apo-A, is clinically important. The results of a number of studies have demonstrated that apo-A-I levels are decreased in subjects with CAD. This observation stresses the protective role of plasma apo-A-I in this patient group.

The results of several studies suggests that by measuring the apo-A-I and apo-A-II levels accurately, it may be possible to predict an individual's prognosis for atherosclerosis, specifically for CAD.

BRIEF SUMMARY OF THE INVENTION

The present invention contemplates monoclonal receptors that immunologically binding with apolipoprotein A, but are free from immunoreaction with and binding to apolipoproteins B, C, D and E. Particularly preferred monoclonal receptors are monoclonal antibodies.

A method of preparing a monoclonal antibody that immunologically binds with an apolipoprotein A constitutes another aspect of the invention. In accordance with that method, a host animal such as a mammal is immunized with an human apolipoprotein A such as HDL or VLDL. Antibody-producing cells of the immunized host are collected as by removing the host's spleen and preparing a suspension of splenocytes. The antibody-producing cells so collected are fused with cells of a myeloma cell line, preferably of the same animal species as the immunized host, and typically in the presence of a cell fusion promoter to form hybridoma cells. The hybridoma cells are diluted and cultured in a medium that does not support growth of unfused myeloma cells such as HT or HAT media. Such dilution and culturing are typically carried out at an initial concentration of about one hybridoma cell per cell growth well. The monocolonal antibodies produced by the culture hybridomas are thereafter assayed for the ability to immunologically bind with apolipoprotein A. A hybridoma whose monoclonal antibodies immunochemically bind with apolipoprotein A is selected and cloned, and is thereafter recovered.

The particularly preferred monoclonal antibodies are produced by hybridomas fused from myelomas denominated P3×63Ag8 (ATCC TIB9), MPC-11 (ATCC CRL 167), S/P 2-O-Ag14 (ATCC CRL 1581), and P3×63Ag8.653 (ATCC CRL 1580).

The above-described method of preparing monoclonal antibodies can include culturing the hybridoma in vitro in a suitable medium and recovering the antibody from the hybridoma supernatant, i.e., a cell culture system. The above method can include injecting the hybridoma into an animal host and recovering the antibodies from ascites fluid of the host.

The present invention also includes the monoclonal antibodies produced by any of the above-described methods, and the above-denominated hybridomas.

A method for assaying the presence of an apolipoprotein A such as HDL constitutes another aspect of the present invention. Here, a monoclonal receptor such as a whole antibody of this invention is provided, and a known amount is admixed with an aliquot of a sample to be assayed for the presence of an apolipoprotein A to form an admixture. The admixture is maintained for a period of time sufficient for the receptor to immunologically bind with an apolipoprotein A present in the sample and form an immunoreactant. The amount of receptor bound in the sample is determined, thereby determining the presence and quantity of the apolipoprotein A such as HDL in the sample.

The methods of the present invention enable the practioner to assay for total HDL present in the sample, as well as for independently assaying for apo-A-I and apo-A-II. The methods also enable the assay of subsets of apo-A-I that are immunologically bound by each of the specific monoclonal receptors of the invention.

The invention further contemplates a diagnostic system such as a kit that includes at least one package containing as an active ingredient an effective amount of the monoclonal receptor (epitope-specific reagent) of this invention which, when introduced into a sample to be assayed (for example, serum), immunologically binding with an apolipoprotein-A such as apo-A-I or apo-A-II, but does not react with other classes of apolipoproteins including apolipoproteins B, C, D and E or non-apolipoproteins, i.e., it is specific.

In panel B, monoclonal antibody A-II-1 was incubated with apo-A-II, and monoclonal antibodies A-I-4, A-I-7 and A-I-9 were incubated with apo-A-I. Results were plotted as the mean counts per minute (cpm) recovered in the precipitate after reaction with an optimal proportion of goat anti-mouse Ig antiserum versus the percent of $^{125}$I-antigen added. For the linear regression, correlation coefficients were equal to or greater than 0.995 for all antigen and antibody combinations shown. The linearity and concordance indicated by the high correlation coefficients (r greater than or equal to 0.995) identified that each antibody reacted with each labeled and nonlabeled antigen pair with the same apparent affinity.

In separate studies, $^{125}$I-HDL labeled by two different methods, namely with either the Bolton-Hunter reagent or by the lactoperoxidase procedure were found to be equivalent in their reactivity for each antibody. In addition, a 1:16 dilution of a polyvalent antisera obtained from a rabbit hyperimmunized with human HDL precipitated 100 percent of 100 ug/ml of $^{125}$I-HDL. Therefore, radioiodination of the antigens did not interfere with the immunoreactivity or account for the inability of these antibodies to bind 100 percent of the labeled antigen.

Figure 8:
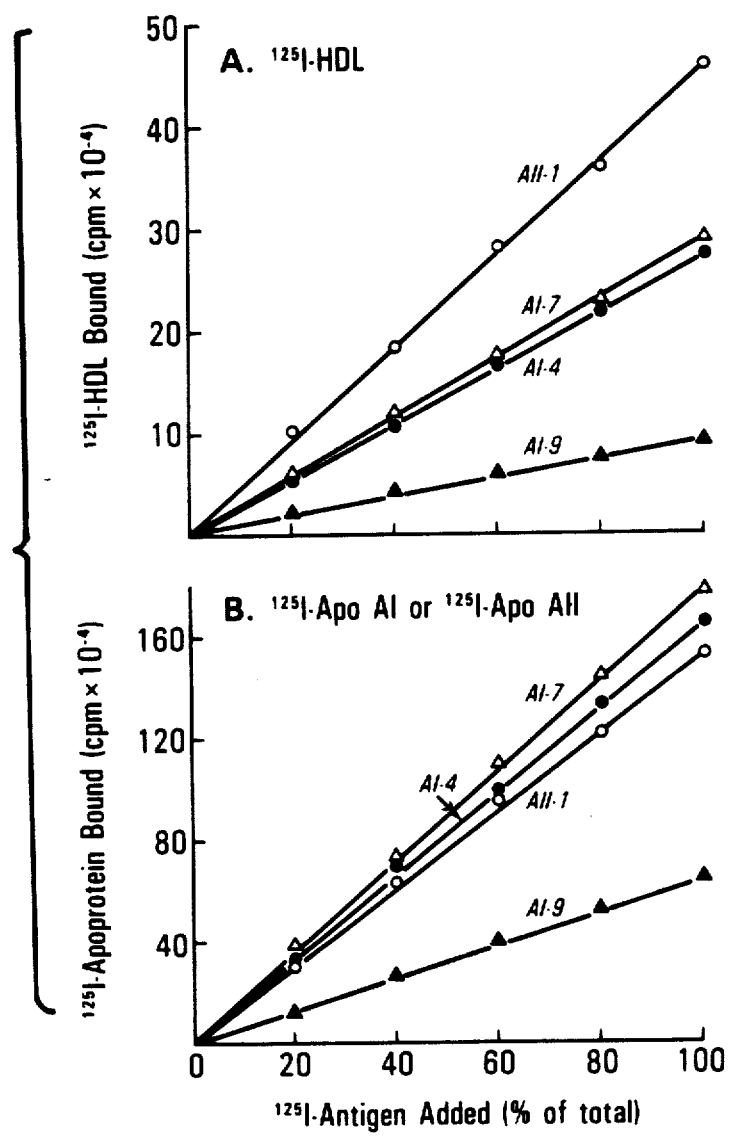

FIG. 8 is a graph showing radioiodination of $^{125}$I-HDL and $^{125}$I-apolipoproteins. The antigens were subjected to mild dissociating conditions that included heat and exposure to detergents to insure that the epitopes recognized by these antibodies were exposed and available for reaction with antibody. Limiting amounts of monoclonal antibodies (Mab) A-I-4, A-I-7, A-I-9 and A-II-1 were added to $^{125}$I-HDL (final concentration 133 ug/ml) that had been incubated at either 4 degrees C. or 52 degrees C. The isolated apolipoproteins, $^{125}$I-apo-A-I and $^{125}$I-apo-A-II were similarly heated before exposure to antibody. Again, no significant increases in antibody binding were observed. In fact, the binding of Mab A-I-7 to $^{125}$I-apo-A-I and antibody Mab A-II-1 to $^{125}$I-apo-A-II was reduced by heating.

To determine if higher temperatures during rather than before antibody exposure would increase binding, reaction mixtures containing $^{125}$I-HDL and antibody were incubated at 4 degrees C., 24 degrees C., 37 degrees C., or 52 degrees C. for up to 18 hours. In no instance did incubation at 37 degrees C. or 52 degrees C. increase binding above that observed at 4 degrees C. or 24 degrees C. and, as noted above, the binding of Mab A-I-7 and Mab A-II-1 to $^{125}$I-HDL was reduced at 52 degrees C.

Figure 9:
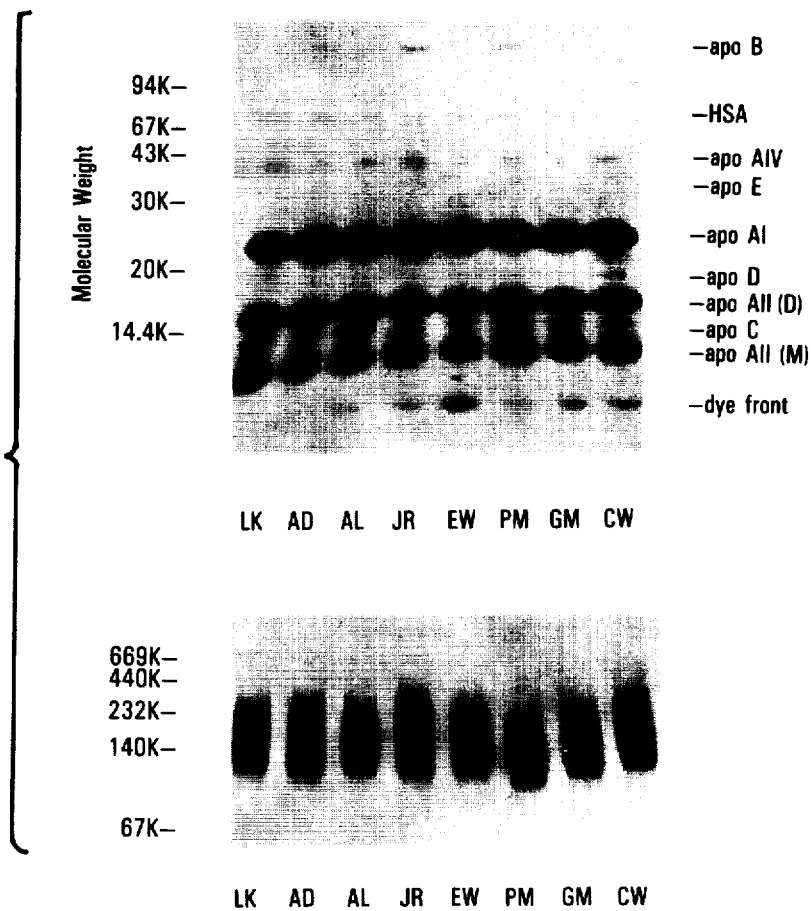

FIG. 9 is a photograph of an autoradiograph showing the polyacrylamide gel electrophoresis of the individual $^{125}$I-HDL ligands. Apolipoproteins and the molecular weights indicated in FIG. 9 were obtained from other lanes of the same gels containing molecular weight markers and unlabeled HDL from a pooled plasma source after staining the gels for protein with Coomassie Brilliant Blue R 250. The sex of the donor, and the specific activity and acid precipitability of the $^{125}$I-HDL ligands, respectively were: LK, female, 5.6 disintegrations per minute per picogram (dpm/pg) and 99.2 percent; AD, female, 6.1 dpm/pg and 99.2 percent; AL, female, 7.1 dpm/pg and 99.2 percent; JR, female, 6.2 dpm/pg and 99.3 percent; EW, male, 6.0 dpm/pg and 99.1 percent; PM, male, 5.8 dpm/ug and 99.0 percent; GM, male, 4.5 dpm/pg and 98.7 percent; and CW, male 6.6 dpm/pg and 99.3 percent.

FIG. 10 is a graph showing the binding capacities of the apo-A antibodies for $^{125}$I-HDL ligands obtained from eight unrelated individuals. The percent of $^{125}$I-HDL that was maximally bound from a pooled HDL source was consistently greatest with Mab A-I-7 (greater than 50 percent), less with antibody A-I-4 (40–50 percent) and lowest with Mab A-I-9 (30–40 percent). This pattern of reactivity was duplicated with the eight $^{125}$I-HDL ligands (final concentration, 15 ng/ml) from the individual donors (FIG. 10A, B and C). Each line represents a different $^{125}$I-HDL ligand. Data from female donors is indicated with solid lines, males in hatched lines. No consistent sex differences were noted. FIG. 10A, RIA with antibody A-I-4; FIG. 10B, RIA with antibody A-I-7; FIG. 10C, RIA with antibody A-I-9; 10D, RIA with antibodies A-I-4, A-I-7 and A-I-9 at a ratio of 1:16:8; FIG. 10E, RIA with antibody AII-1; and FIG. 10F, RIA with antibodies A-I-4, A-I-9 and A-II-1 at a ratio of 1:16:8.

DETAILED DESCRIPTION OF THE INVENTION

I. GENERAL DISCUSSION

The term "receptor" as used herein is meant to indicate a biologically active molecule that immunologically binds to (or with) an antigen. Such binding typically occurs with an affinity of about $10^5$ liters per mole and is specific interaction of the epitope of the antigen with the Fab portion of the receptor.

A receptor molecule of the present invention is an intact antibody protein, substantially intact antibody or an idiotype-containing polypeptide portion of an antibody (antibody combining site) in subtantially pure form, such as in ascites fluid or serum of an immunized animal. The terms "receptor" and "monoclonal receptor" are used interchangeably herein in a generalized sense for a molecular entity that contains the antibody combining site of a monoclonal antibody of this invention. The terms "antibody", "monoclonal antibody" and "Mab" are utilized interchangeably herein for a whole antibody of this invention.

The term "ligand" as used herein is meant to indicate a molecule that contains a structural part that is immunologically bound by a specific receptor to form an immunoreactant. A ligand used in the present invention is an apolipoprotein A-containing entity such as a radioiodinated HDL antigen adhered to a solid matrix as described in the radioimmunoassay described hereinafter.

Biological activity of a receptor molecule is evidenced by the immunologic reaction of the receptor to its antigenic ligand upon their admixture in an aqueous medium to form an immunoreactant, at least at physiological pH values and ionic strengths. Preferably, the receptors also bind to the antigenic ligand within a pH value range of about 5 to about 9, and at ionic strengths such as that of distilled water to that of about one molar sodium chloride.

Idiotype-containing polypeptide portions (antibody combining sites) of antibodies are those portions of antibody molecules that contain the idiotype and bind to the ligand, and include the Fab, Fab' and F(ab')$_2$ portions of the antibodies. Fab and F(ab')$_2$ portions of antibodies are well known in the art, and are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy chain portions as with mercaptoethanol, and then alkylation of the resulting protein mercaptan with reagent such as iodoacetamide. Intact antibodies are preferred, and will be utilized as illustrative of the receptor molecules of this invention.

A "monoclonal receptor" (Mab) is produced by clones of a single cell called a hybridoma that produces (secretes) but one kind of receptor molecule. "Polyclonal" antibodies (Pab) are antibodies produced by clones derived from different cells that secrete different antibodies that bind to a plurality of epitopes of the immunogenic molecule. The preparation of Pab is discussed hereinafter as part of the production of Mabs.

The hybridoma cell is fused from an antibody-producing cell and a myeloma or other self-perpetuating cell line. Such receptors were first described by Kohler and Milstein, Nature, 256, 495 (1975), which description is incorporated herein by reference. Monoclonal receptors are typically obtained from the supernatants of hybridoma cell cultures, or, alternatively, from ascites fluid or other body fluids obtained from non-human, warm blooded host animals into which the hybridoma cells were introduced.

Antibodies are secreted by specialized cells called plasma cells and to a quantitatively lesser degree by their precursor B cells (bone marrow-derived lymphocytes). Each B cell or plasma cell secretes one type of antibody having a single specificity, so various antibodies of different specificites are each secreted by different B cells and their derivative plasma cells. These B cells may be cloned to provide a source of single antibodies. However, these cells die in a few days in culture media and must be made relatively "immortal" so that a supply of the desired antibodies may be obtained. This is accomplished by removing the B cells and plasma cells from the animal, typically from the spleen, fusing them with a cancerous or myeloma cell to form a somatic cell hybrid (hybridoma), and then cloning and propagating the hybridoma.

The antibody-producing cells that are employed may be obtained from a non-human host animal immunized by injection of an immunogen, in this instance a human apolipoprotein A, typically followed by one or more booster injections with the same immunogen. The spleen is isolated after a sufficient time period has elapsed for the host to produce antibodies, this is typically about one month to about three months after the first immunization.

Non-human, warm blooded animals usable in the present invention as hosts may include poultry (such as a chicken or a pigeon), a member of the ratitae bird group (such as an emu, ostrich, cassowary or moa) or a mammal (such as a dog, cat, monkey, goat, pig, cow, horse, rabbit, guinea pig, rat, hamster or mouse). Preferably, the host animal is a mouse or rabbit.

It is preferred that a myeloma cell line be from the same species as the antibody-producing cells. Therefore, fused hybrids such as mouse-mouse hybrids [Shulman et al., *Nature*, 276, 269 (1978) or rat-rat hybrids (Galfre et al., *Nature*, 277, 131 (1979)] are typically utilized. However, some rat-mouse hybrids have also been successfully used in forming hybridomas [Goding, "Production of Monoclonal Antibodies by Cell Fusion", in *Antibody as a Tool*, Marchalonis et al. eds., John Wiley & Sons Ltd., 273-289 (1982), hereinafter Marchalonis et al.]. Suitable myeloma lines for use in the present invention include MPC-11 (ATCC CRL 167), P3×63-Ag8.653 (ATCC CRL 1580), Sp 2/0-Ag14 (ATCC CRL 1581), P3×63Ag8U.1 (ATCC CRL 1597), Y3-Ag12.3 (deposited at Collection Nationale de Cultures de Microorganisms, Paris, France, number I-078 and P3×63Ag8 (ATCC TIB9). Myeloma line P3×63-Ag8.653 is preferred for use in the present invention.

Monoclonal anti-apolipoprotein A receptors were formed as described herein from murine (mouse) splenocytes fused with murine myeloma cells. The polyclonal anti-apolipoprotein A antibodies described were formed from rabbits. The hybridomas that produce the monoclonal anti-apo-A-I and anti-apo-A-II receptors of this invention were given the following designations for reference purposes and were deposited with the American Type Culture Collection (ATCC), Rockville, Maryland on Mar. 5, 1985 under the following ATCC accession numbers.

| Hybridoma | Mab | ATCC Accession Number |
|---|---|---|
| HA61 H112F3.1A11 | A-II-1 | HB 8743 |
| 611 AV63C2.1F1 | A-I-4 | HB 8744 |
| HA60 HA22GF.5F8 | A-I-7 | HB 8745 |
| HA62 HA227A2.7D3 | A-I-9 | HB 8741 |

Receptors are typically utilized along with an indicator labeling means or "indicating group" or a "label".

The indicating group or label is utilized in conjunction with the receptor as a means for determining the extent of a reaction between the receptor and the antigen.

The terms "indicator labeling means", "indicating group" or "label" are used herein to include single atoms and molecules that are linked to the receptor or used separately, and whether those atoms or molecules are used alone or in conjunction with additional reagents. Such indicating groups or labels are themselves well-known in immunochemistry and constitute a part of this invention only insofar as they are utilized with otherwise novel receptors, methods and/or systems.

The indicator labelling means can be a fluorescent labelling agent that chemically binds to antibodies or antigens without denaturing them to form a fluorochrome (dye) that is a useful immunofluorescent tracer. Suitable fluorescent labelling agents are fluorochromes such as fluorescein isocyanate (FIC), flourescein isothiocyanate (FITC), dimethylamino-naphthalene-S-sulphonyl chloride (DANSC), tetramethylrhodamine isothiocyanate (TRITC), lissamine, rhodamine B200 sulphonyl chloride (RB 200 SC) and the like. A description of immunofluorescence analysis techniques is found in Marchalonis et al., "Immunofluorescence Analysis", 189-231, supra, which is incorporated herein by reference.

The indicating group may also be an enzyme, such as horseradish peroxidase (HRP) or glucose oxidase, or the like. Where the principal indicating group is an enzyme such as HRP or glucose oxidase, additional reagents are required to visualize the fact that a receptor-ligand complex has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-6-sulfonic acid) (ABTS).

An exemplary radiolabelling agent is a radioactive element that produces gamma ray emissions. Elements which themselves emit gamma rays, such as $^{124}I$, $^{125}I$, $^{128}I$, $^{131}I$, $^{132}I$, and $^{51}Cr$ represent one class of gamma ray emission-producing radioactive element indicating groups. Particularly preferred is $^{125}I$. Another class of useful indicating groups are those elements such $^{11}C$, $^{18}F$, $^{15}O$ and $^{13}N$ which themselves emit positrons. The positrons so emitted produce gamma rays upon encounters with electrons present in the animal's body. Also useful is a beta ray emitter, such as $^{111}$indium.

A preferred radioactively labeled monoclonal receptor may be prepared by culturing hybridoma cells in a medium containing radioactive amino acids, as is well known, as well as by isolating the monoclonal receptor and then labelling the monoclonal receptor with one of the above radioactive elements as described in U.S. Pat. No. 4.,381,292 to Bieber and Howard, incorporated herein by reference.

Specific indicating means linked to reagents that react with the receptors of this invention are discussed hereinafter.

Four previously identified monoclonal antibodies that bind to apolipoproteins A of human plasma HDL were obtained from their respective hybridomas and characterized. Each of these antibodies was specific for the apolipoproteins of human HDL, based on binding to delipidated and isolated apolipoproteins of HDL after transfer to nitrocellulose and binding of the soluble apolipoproteins in fluid phase.

The vast majority of the monoclonal antibodies obtained by immunization of mice with native human HDL were specific for human apo-A-I, suggesting greater immunogenicity of human apo-A-I for BALB/c mice. This difference in immunogenicity between apolipoproteins A-I and A-II was observed also when the isolated apolipoproteins were used as immunogens. Thus, of the four antibodies characterized in this study, three were specific for three separate epitopes on apo-A-I. Only a single apo-A-II-specific antibody was obtained and characterized.

Human plasma HDL of density 1.063-1.21 g/ml represents a heterogenous mixture of HDL particles that differ with respect to both lipid and protein composition. Using the hybridoma-produced antibodies of this invention that define apo-A-I-specific and apo-A-II-specific epitopes, immunochemical heterogeneity of HDL was clearly evident.

Figure 2:
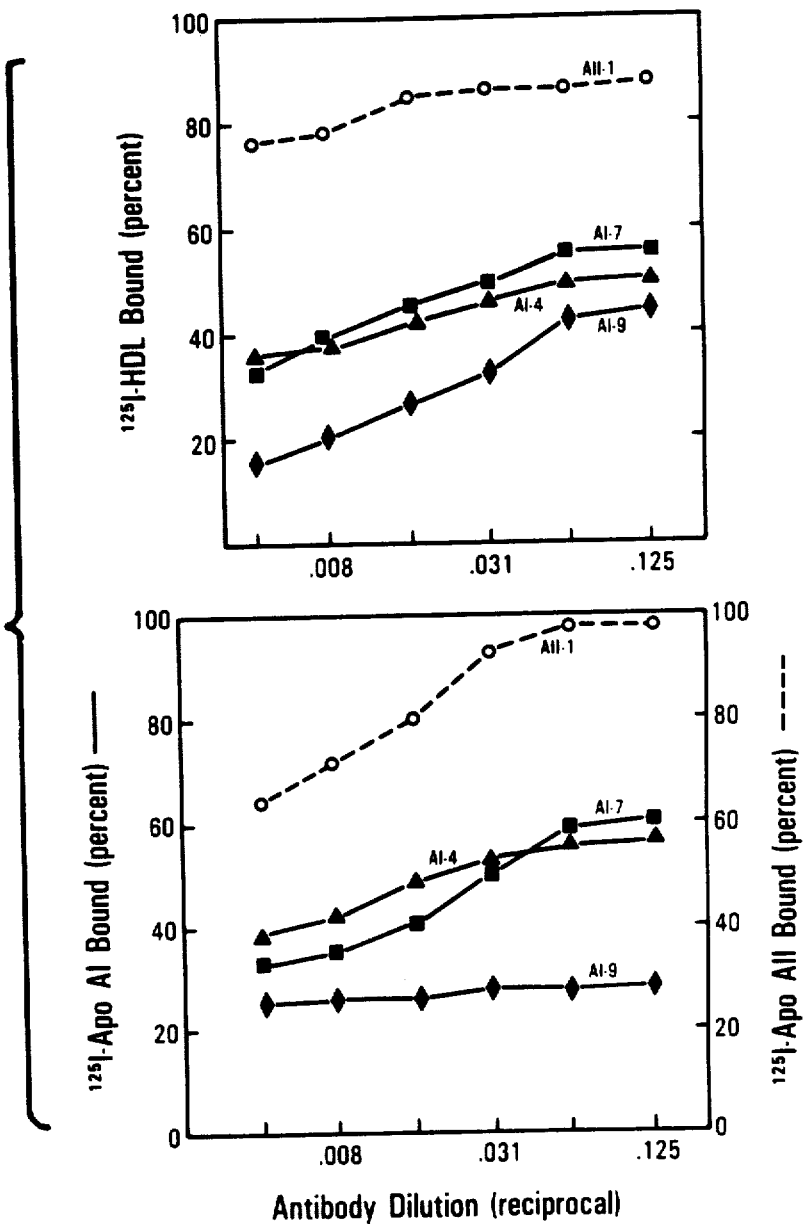
FIG. 2 is a graph of data illustrating maximum binding capacity of mouse ascites fluids containing human apo-A-I- and apo-A-II-specific monoclonal receptors (antibodies). The upper portion of the figure shows binding of $^{125}$I-HDL. The lower portion of the figure is a graph showing data of binding of $^{125}$I-apo-A-I or $^{125}$I-apo-A-II. The fluid-phase RIAs were incubated for 18 hours at 4 degrees C. and contained $^{125}$I-HDL, $^{125}$I-apo-A-I, or $^{125}$I-apo-A-II at final concentrations of 66.7, 33.3, and 33.3 nanograms per milliliter (ng/ml), respectively. The coefficient of variation for all data points was less than 10 percent.

Solid-phase immunoassays permitted analysis of antibody specificity, but with fluid-phase assays it was possible to analyze the heterogeneity of molecules with respect to expression of individual epitopes. It was found that not all HDL particles expressed the defined apo-A-I and apo-A-II epitopes that could be bound by a given apo-A-I-specific antibody. The unbound HDL contained apo-A-I and HDL, indicating heterogeneity of epitope display by apo-A-I on different particles (FIG. 2).

Figure 3:
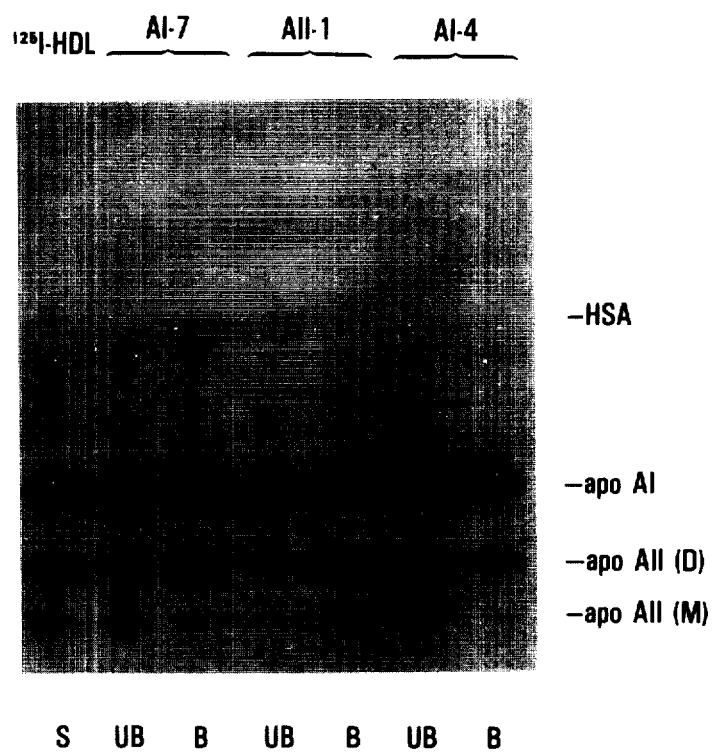
FIG. 3 is a photograph of a 24 hour autoradiograph after gel electrophoresis for determining apolipoprotein composition of the antibody bound and unbound portions of $^{125}$I-HDL. The $^{125}$I-HDL was contacted and maintained in contact (incubated) with monoclonal antibodies A-I-7, A-II-1, and A-I-4 in antibody excess for 18 hours at 4 degrees C. followed by precipitation of the monoclonal antibody with optimal proportions of goat anti-mouse Ig antiserum. The precipitates containing the bound fractions (B) and the supernatants containing the unbound fractions (UB) were recovered, dissolved in 1 percent sodium dodecyl sulfate (SDS), and electrophoresed along with the starting $^{125}$I-HDL (S) on a 7.5–20 percent polyacrylamide gradient pore gel in the presence of 0.1 percent SDS. The notations are as follows: HSA represents human serum albumin; (D) represents apo-A-II dimer and (M) represents apo-A-II monomer.

The existence of at least two types of HDL; i.e., particles containing apo-A-I and apo-A-II, and particles containing apo-A-I but no apo-A-II, was verified with monoclonal antibody A-II-1. Whereas this apo-A-II-specific antibody bound only a subset of total HDL, it did bind all apo-A-II (FIG. 2). The unbound HDL was devoid of detectable apo-A-II, appearing to contain only apo-A-I (FIG. 3). Thus, all HDL particles possessing an apo-A-II chain expressed this A-II epitope.

Heterogeneity of epitope expression by isolated apo-A-I was readily evident. None of the apo-A-I-specific antibodies was able to bind all apo-A-I molecules, either as HDL or soluble apo-A-I. The inability of each of the anti-apo-A-I antibodies to identify its complementary epitope on all A-I apolipoprotein chains was examined. First, technical issues were excluded such as affinity, quantity of available antibody, or radioiodination of the ligands. Second, it was demonstrated that the antibodies did not selectively bind different apo-A-I isoforms. Third, the use of dissociating conditions (e.g., heat and nonionic detergents) designed to mobilize and expose cryptic epitopes of the apolipoprotein on either HDL or the isolated soluble state did not result in a significant increase in the capacity of antibody to bind all molecules.

Immunochemical heterogeneity of epitope expression by apo-A-I organized on HDL was further supported by the demonstration that the combination of three apo-A-I-specific antibodies could bind a greater relative proportion of HDL than any single antibody (Table I, hereinafter). Thus, the three apo-A-I epitopes recognized by the anti-apo-A-I differed, and some particles existed that expressed only one or another of these three epitopes.

Apo-A-I occurs predominantly, if not virtually entirely, associated with lipid. The heterogeneity of epitope expression was determined by lipoprotein-associated apo-A-I.

The possibility that these antibodies distinguished individual epitopes of apo-A-I that were present or not on the basis of allotypic (genetically determined individual differences) or sex differences in apo-A-I was examined. For those studies, HDL was isolated from single individual normo-lipidemic subjects. Compared with pooled plasma, HDL isolated from the plasmas of four unrelated normal donors of each sex had similar patterns of heterogeneous epitope expression.

Because these antibodies did not appear to identify allotypic or sex differences between individuals in their apo-A-I molecules, the existence of multiple apo-A-I genes was considered since differential gene regulation, or differential sites or rates of metabolism might account for the observed heterogeneity of apo-A-I. It appears that there is a single apo-A-I gene (Karathanasis et al., *Proc. Natl. Acad. Sci. USA*, 80, 6147–6151 (1983). Alternative splicing of the gene has not been described but has not been examined.

Also, each of the epitopes is expressed by the different apo-A-I charge isoforms. Thus, it was determined whether the apo-A-I antibodies selectively distinguished apo-A-I on HDL that was derived from different known major synthetic sources such as the liver and the intestine. Thoracic duct lymph was used as an enriched source of intestinal apo-A-I. The medium from human Hep G2 hepatoma cultures provided a source of pure hepatic apo-A-I.

Both the hepatic and intestinal apo-A-I contained molecules expressing epitopes bound by antibodies A-I-7 and A-I-9; i.e., A-I-7 and A-I-9 epitopes. In addition, plasma VLDL fractions that provide a source of both hepatic and intestinal (chylomicron remnant) apo-A-I expressed only the epitope bound by antibody A-I-9. Therefore, the results are not consistent with epitope differences based on different synthetic sources.

The hypothesis that the three apo-A-I epitopes distinguish between molecules differently organized on different HDL particles was in part substantiated by separation of HDL on the basis of the physical properties of density and charge. However, because density and chromatofocusing fractions differed quantitatively but not absolutely in the expression of individual apo-A-I epitopes, these methods did not entirely resolve the responsible subsets of HDL. Rather, they facilitate only enrichment or relative depletion of particles expressing individual apo-A-I epitopes.

Physical fractionation of native HDL is unlikely to result in complete segregation of specific apo-A-I epitopes expressed by apo-A-I on HDL, since HDL particles appear not to exist that exclusively contain only apo-A-I organized in a single conformational format. However, immunochemical separation may provide new information. Recent studies of immunopurified HDL have shown that ultracentrifugation can alter HDL structure and suggest that additional studies of the immunochemical properties of HDL should be directed at the HDL particle as it exists in plasma [McVicar et al., *Proc. Natl. Acad. Sci. USA*, 81, 356–1360 (1984)].

There is no reason to assume that conformational variation will be identical for lipid-free and lipid-associated apo-A-I. For example, protein-protein interactions resulting in the formation of soluble oligomers of lipid-free apo-A-I have been observed in preliminary studies to influence the degree of expression of epitope A-I-4; whereas protein-lipid or lipoprotein interactions appear to have a similar influence. Studies of the HDL density and chromatofocusing subfractions demonstrate that apo-A-I is not organized the same on different HDL particles.

The lighter, larger cholesterol-rich HDL (HDL$_2$-like) that are enriched in apo-A-I relative to other apolipoproteins are rich in apo-A-I that express predominantly the A-I-9 epitope. In contrast, the more dense, smaller, cholesterol-poor HDL which contain apo-A-II and other minor apolipoproteins are rich in apo-A-I that express predominantly the A-I-7 epitope. Because these two types of HDL particles may represent different metabolic states of HDL, the different apo-A-I conformations on HDL may serve to direct HDL particles to their proper enzymatic or cellular sites.

Some methods of quantitative analysis of plasma HDL have employed immunologic assays for apolipoproteins A-I or A-II. The immunochemical properties of these apolipoproteins as evident from analysis with polyclonal antibodies have indicated the existence of unusual and distinctive properties. The reactivity of apo-A-II-specific antisera is for the most part comparable for apo-A-II whether in free solution or associated with HDL [Mas et al., Biochemistry, 14, 4127–4131 (1975)].

However, the HDL density class is composed of at least two types of HDL particles; i.e., those possessing both apo-A-I and apo-A-II, and those containing apo-A-I, but no apo-A-II. Because all HDL particles appear to contain apo-A-I, immunologic analyses of apo-A-I have been herein used in quantitating total plasma HDL. A caveat is the difference in the ability of various antisera to detect all apo-A-I in HDL or plasma. The reasons offered for this discrepancy have centered around the hypothesis that some apo-A-I epitopes on native HDL are sterically occult.

As noted before, hybridoma cell lines that secrete human HDL-binding monoclonal antibodies were prepared to examine this molecular aberration, to determine if the apparent immunochemical heterogeneity of HDL and its apolipoproteins is valid, and to obtain precise immunochemical reagents that permit quantitation of all HDL particles in plasma as well as defined subsets of HDL.

Three mouse monoclonal antibodies (Mab's) specific for human apolipoprotein (apo) A-I and one specific for human apo-A-II that were prepared have been highly characterized and their binding of high density lipoprotein (HDL) particles in solution was determined. The apo-A-II-specific antibody bound 85 percent of $^{125}$I-HDL and 100 percent of soluble $^{125}$I-apo-A-II. However, none of the apo-A-I-specific antibodies bound more than 60 percent of either HDL or soluble apo-A-I.

These results suggested the existence of intrinsic immunochemical heterogeneity of apo-A-I both as organized on HDL as well as in free apo-A-I in solution. The validity of this observed heterogeneity was supported by demonstrating that (i) increased binding of HDL occurred when each of the apo-A-I antibodies was combined with another to form an oligoclonal antibody mixture, and (ii) approximately 100 percent binding of HDL occurred when any two apo-A-I antibodies (antibodies denominated A-I-4 and A-I-7; i.e., Mab A-I-4, of hybridoma 611 AV63C2.1F1 (ATCC HB 8744) and Mab A-1-7, of hybridoma HA60 HA22GF.5F8 (ATCC HB 8745) were combined with the single apo-A-II antibody Mab A-II-1 produced by hybridoma HA61 H112F3.1A11 (ATCC HB 8743).

To understand the basis for the heterogeneity of the expression of apo-A-I epitopes on HDL, two hypotheses were examined. The first hypothesis that these apo-A-I antibodies distinguished apo-A-I molecules from different synthetic sources was not substantiated. Two of the antibodies bound epitopes on apo-A-I molecules in both thoracic duct lymph as an enriched source of intestinal HDL and the culture supernatants of the hepatic cell line Hep G2 as a source of hepatic HDL.

From the assays of this invention, it has been shown that the monoclonal antibodies identified differences in the expression of apo-A-I on HDL subpopulations that were distinguished on the basis of size or net particle charge; i.e., organizational heterogeneity appeared to provide the best available explanation for the immunochemical heterogeneity of apo-A-I in HDL.

Relative differences in the expression of three distinct apo-A-I epitopes were demonstrated in HDL subpopulations obtained by either density gradient ultracentrifugation or chromatofocusing. In light of these studies, it is concluded that there is intrinsic heterogeneity in the expression of intramolecular loci representing the apo-A-I epitopes identified by the monoclonal antibodies of this invention. Such heterogeneity must be considered in analysis of the biology and physiology of apo-A-I and lipoprotein particles bearing this chain as well as any attempt to immunologically quantitate or characterize HDL.

II. ASSAY METHODS

The monoclonal receptor molecules of the present invention are particularly useful in methods for assaying the presence and amount of an apolipoprotein A such as that of HDL in a sample to be assayed such as blood, serum or plasma. As noted hereinafter, the presence and amount of HDL and soluble apolipoproteins A may also be assayed in other body fluids such as lymph, and in in vitro materials such as hepatic cell cultures and the like.

Useful solid and liquid phase assay methods are discussed hereinafter. However, the invention is not so limited. Further, while the particularly described assay methods utilize a radioactive element and determination of receptor bound in apolipoprotein A/receptor-containing immunoreactants (radioimmunoassay; RIA), the present invention is also not specifically limited to such assays. Additional assay methods are described hereinbelow with particular emphasis on solid phase immunoassay methods.

Solid phase assay methods are comprised of an antigen or a receptor of this invention affixed to a solid matrix as a solid support.

The antigen or receptor is typically affixed to the solid matrix by adsorption from an aqueous medium, although several modes of adsorption, as well as other modes of affixation, well known to those skilled in the art may be used. Exemplary of such modes are the reaction of the receptor or antigen with the reactive carboxyl functionality produced by the reaction of cyanogen bromide with glucose-containing matrices such as cross-linked dextrans or cellulosics, glutaraldehyde linking as discussed hereinafter in conjunction with latex particles, and the like.

Useful solid matrices are well known in the art. Such materials include the cross-linked dextran available under the trademark SEPHADEX from Pharmacia Fine Chemicals (Piscataway, N.J.); agarose; beads of glass; polystyrene beads about 1 micron to about 5 millimeters in diameter available from Abbott Laboratories of North Chicago, Ill.; polyvinyl chloride, polystyrene, cross-linked polyacrylamide, nitrocellulose or nylon-based webs such as sheets, strips or paddles; or tubes, plates or the wells of a microtiter plate such as those made from polystyrene or polyvinylchloride.

Latex particles useful in agglutination-type assays are also useful solid matrices. Such materials are supplied by the Japan Synthetic Rubber Company of Tokyo, Japan, and are described as carboxy-functional particles dispersed in an anionic soap. Typical lots of such particles have an average diameter of 0.308 microns, and may have an average carboxy-functional group distribution of about 15 to about 30 square Angstroms per carboxy group.

Prior to use, the particles are reacted with a diamine such as 1,3-diamino-2-propanol to form a plurality of amide bonds with the particle carboxy groups while maintaining free amine groups. The free amines are thereafter reacted with a dialdehyde such as glutaraldehyde and the receptor or antigen to form Schiff base reaction products. The Schiff base reaction products are thereafter reduced with a water-soluble reductant such as sodium borohydride to provide a useful solid support.

Those skilled in the art will understand that there are numerous methods for solid phase immunoassays that may be utilized herein. Exemplary, useful solid phase assays include enzyme-linked immunosorbant assays (ELISA) and fluorescence immune assays (FIA), in addition to the specifically discussed RIA. However, any method that results in a signal imparted by the reaction of apolipoprotein A with a receptor of this invention is considered. Each of those assay methods may employ single or double antibody techniques in which an indicating means is utilized to signal the immunoreaction, and thereby the binding of an apolipoprotein A that is to be assayed with a receptor of this invention. Exemplary techniques may be found explained in Maggio, *Enzyme Immunoassay*, CRC Press, Cleveland, Ohio (1981); and in Goldman, *Fluorescent Antibody Methods*, Academic Press, New York, N.Y. (1980).

Broadly, the presence of an apolipoprotein A such as that of human HDL in a sample to be assayed includes the following steps.

(a) An effective amount of a monoclonal receptor of this invention whose antibody combining site immunoreacts with and binds to human apolipoprotein A, but is free from immunoreaction with and binding to human apolipoproteins B, D, D, and E, or other known proteins or ligands is provided. The receptor is also free from immunological binding with any other protein or ligand found in plasma or serum of normal individuals. This is typically accomplished by using an aliquot of an appropriate hybridoma supernatant or ascites.

The effective amount of receptor will differ, inter alia, with the particular receptor used, and with the particular assay method utilized, as is well known. Also well known is the ease with which the effective amount may be determined using standard laboratory procedures by one skilled in preparing such assays.

(b) A known amount of the receptor is admixed with aliquot of a sample to be analyzed for the presence of an apolipoprotein A such as that of human HDL, to form an admixture. The admixture so formed may be a liquid admixture as in the liquid phase RIA described hereinafter, or that admixture may be a solid/liquid admixture as where a solid support is utilized.

(c) In either event, the admixture so formed is maintained for a predetermined period of time from minutes to hours, such as about 90 minutes to about 16–20 hours at a temperature of about 4 degrees to about 45 degrees C. that is sufficient for the receptor to immunoreact with and bind to apo-A present in the sample, and form an immunoreactant.

(d) The amount of receptor bound in the immunoreactant is then determined to thereby determine the amount of apo-A as in HDL present in the sample. That amount may be zero, thereby indicating that no apo-A is present in the sample, within the limits that may be detected.

Individual receptors of this invention may be utilized or the individual receptor molecules may be admixed for use. The particular receptor or combination to use for assaying for the presence of a particular apo-A-containing molecule may be determined from the data of the RESULTS section (IV) that follows. Thus, one may select a receptor that immunoreacts with and binds to apolipoprotein A-I, or A-II, or both A-I and A-II.

For example, if it is desirable to analyze only apo-A-II molecules, the receptor of choice (A-II-1) is that produced by the hybridoma denominated HA61 H112F3.1A11 (ATCC HB 8743). If only apo A-I subsets are desired, then each of the three different receptors (A-I-4, A-I-7 or A-I-9) provide a reagent for each subset defined by these receptors. Where the total HDL present in a sample is desired, a mixture containing A-II-1 receptors plus receptors produced by any two of the other three hybridomas of this invention, i.e., receptors denominated A-I-4, A-I-7, or A-I-9 (from hybridomas 611 AV63C2.1F1, ATCC HB 8744; HA60 HA22GF.5F8, ATCC HB 8745; or HA62 HA22-7A2.7D3, ATCC HB 8741; respectively).

In one embodiment of the above, general method, an apolipoprotein A that is bound by the receptor used in the method such as human HDL is provided affixed to a solid matrix as a solid support antigen. The admixture of step (c), above, is present as a liquid admixture, and is admixed with the solid support to form a solid/liquid phase admixture. That solid/liquid phase admixture is maintained for a predetermined time period such as about 16–18 hours at 4° C. that is sufficient for the receptor molecules in the liquid admixture to immunoreact with and bind to the antigen and form an immunoreactant. The solid and liquid phases are separated, and the solid phase is usually rinsed to remove non-specifically bound receptor molecules. The amount of receptor molecules bound (specifically) in the immunoreactant is then determined.

Where the sample is free from apo-A molecules, the amount of receptor in the solid phase immunoreactant is relatively high. Conversely, where there is a relatively large amount of apo-A molecules as where there is a large amount of human HDL present in the sample, the amount of bound receptor is relatively lower. Quantitative comparison of the result obtained with separately obtained control results provides quantitation of the amount of apo-A in the sample.

The determination of the amount of receptor bound may be by means of an indicating means-containing reagent that reacts with the bound receptor but does not react with the solid support antigen such as $^{125}$I-labeled goat anti-mouse Ig, where the receptors are mouse antibodies. The receptor may itself include a linked indicating means such as a radioactive element or an enzyme that signals the formation of an immunoreactant, or an added ligand specific for another indicating receptor.

In another embodiment of the general method, the sample to be assayed may be affixed to a solid matrix as a solid support antigen prior to forming the admixture described in the general method in step (b), above. It is understood that while several entities from the sample may become affixed to the solid support, the useful solid support antigen includes those entities such as HDL that contain apolipoprotein A.

The sample may be affixed in several ways as are known, and described previously. One exemplary method is by adsorption as is discussed in connection with the solid phase RIA described hereinafter.

When the sample is affixed to the solid support prior to formation of the admixture of step (b), the admixture formed in that step is a solid/liquid admixture in which the solid phase is the solid support antigen and the liquid phase is the aqueous composition that includes a receptor of this invention. The solid/liquid phase admixture is maintained as already described, and is separated prior to determining the amount of receptor that is bound in the immunoreactant. The separated solid phase is typically rinsed prior to that determination being made, as discussed before.

A convenient way to determine the amount of receptors bound in the above-described method utilizes an indicating means-containing reagent that reacts with the bound receptors to form a bound reaction product, but does not bind to the solid support antigen. The indicating means of the reagent signals the presence of the bound receptor.

A known amount of a liquid composition including such a reagent is admixed with the separated solid phase to form a second solid/liquid admixture. That admixture is maintained for a predetermined period of time sufficient for the reagent to react with the bound receptor of the immunoreactant and form a bound reaction product.

The solid and liquid phases are thereafter separated as described before and the amount of bound reaction product is determined.

In the case of the specifically disclosed RIA, the reagent was goat anti-mouse antibodies that immunoreact with and bind to the mouse-derived receptor molecules. That reagent included linked iodine-125 atoms (indicator) whose gamma radiation provided the signal that bound receptor was present in the solid phase, and consequently that an human apolipoprotein A was present in the sample.

The indicating means may also be an enzyme or a fluorescent molecule that is linked to the reagent for use in an enzyme-linked immunosorbent assay (ELISA) or fluorescence immunoassay (FIA), respectively.

For an ELISA, typically used enzymes linked to the reagent as a signalling means include horseradish peroxidase, alkaline phosphatase and the like. Each of those enzymes is used with a color-forming reagent or reagents (substrate) such as hydrogen peroxide and o-phenylenediamine; and p-nitrophenyl phosphate, respectively.

Enzyme-linked antibody (conjugate) reagents of one animal raised to the antibodies of another animal such as peroxidase-linked rabbit anti-goat and goat anti-mouse antibodies, as well as phosphatase-linked rabbit anti-goat, and rabbit anti-mouse antibodies are commercially available from several suppliers such as Sigma Chemical Company of St. Louis, Mo. Those indicating means-containing reagents may be used where the receptor utilized has an Fc portion of the "other animal", e.g., goat and mouse.

Similar assays may also be carried out using fluorochrome dyes linked to an antibody as an indicating means-containing reagent to signal the presence of receptors bound in an immunoreaction product The fluorochrome dye is typically linked by means of an isothiocyanate group to form the conjugate. Exemplary fluorochrome dyes include fluorescein isothiocyanate (FITC), rhodamine B isothiocyanate (RITC) and tetramethylrhodamine isothiocyanate (TRITC). Conjugates such as FITC-linked rabbit anti-mouse, goat anti-mouse, goat anti-rabbit and sheep anti-mouse antibodies are commercially available from several sources such as Sigma Chemical Company.

In addition to the RIA, ELISA and FIA techniques for determining the presence of receptors of this invention bound to an antigen in an immunoreactant, other well known techniques are also available. In one technique, protein A of *Staphylococcus aureus* linked to a signalling means such as $^{125}I$ is utilized to determine the presence of the receptors bound to the solid support.

In another technique, biotin linked to an antibody reagent is utilized to signal the presence of the immunoreactant in conjunction with avidin that is itself linked to a signalling means such as horseradish peroxidase. Biotin-linked antibody conjugates such as biotin-linked goat anti-rabbit, goat anti-mouse and rabbit anti-goat IgG's are commercially available from Polysciences, Inc. of Warrington, PA. Avidin-FITC, avidin-RITC, avidin-peroxidase and avidin-alkaline phosphatase are also available commercially from Polysciences, Inc. for use with the biotin-linked antibody conjugates to provide the signal. Still other techniques are well known to those skilled in this art.

In a still further embodiment of the before-described method, the admixture formed in step (b) is a liquid admixture; i.e., the sample to be assayed and the receptors are admixed in a liquid composition that is typically aqueous. That admixture includes a known amount of a radiolabeled apolipoprotein A-containing competitive antigen such as HDL, or free human apo-A-II or apo-A-I.

Where such a liquid phase admixture is used, the amount of receptor bound in the immunoreactant may be determined by admixing an excess of an antibody that immunoreacts with, binds to and precipitates the receptors with the liquid phase admixture, to form a second liquid phase admixture. The precipitating antibody so used does not immunoreact with, bind to or precipitate the apolipoprotein being assayed for or the competitive antigen. An exemplary antibody is the $^{125}I$-goat anti-mouse Ig used in a RIA described hereinafter.

The second liquid phase admixture is maintained for a predetermined period of time suffcent for the admixed antibody to immunoreact with, bind to and precipitate the receptors of the immunoreactant, and form a precipitate and a supernatant.

The precipitate and supernatant are separated; and the radioactivity present in the precipitate is measured. That measurement, when compared to control valves obtained with known amounts of assayed apolipoprotein A, radioactive competitive antigen, receptor and precipitating antibody, may be used to provide the amount of receptor bound in the immunoreactant, and thereby the amount of apolipoprotein A present in the sample assayed.

A still further aspect of the invention contemplates the use of the before-mentioned latex particles as a solid matrix of a solid support. In an exemplary method, a receptor of this invention is affixed to the latex particles, as described before, prior to the admixture of step (b) of the previously described, general method.

The sample to be assayed is admixed in an aqueous medium with those particles to form a solid/liquid phase admixture that is a dispersion of solid latex particles in an aqueous medium. The admixture is maintained for a time period sufficient for an immunoreactant to form, which formation causes the latex particles to agglutinate.

The time required for the latex particles to agglutinate is measured. That measurement provides a determination of the amount of receptor bound in an immunoreactant, and thereby the presence and relative amount of apolipoprotein A present in the sample by comparison with values obtained with controls.

Similar agglutination methods may be performed with red blood cells (hemagglutination) or with other agglutinatable particles or cells following the above steps.

Still further assay methods within the before-described general method may also be employed. Each of those methods differs from those previously described by the manner in which the amount of immunochemical binding is determined.

One group of such methods utilizes optical measurements for that determination. In one exemplary procedure, a liquid admixture is formed in before-described steps (b) and (c) and the turbidity of the liquid admixture is measured and compared to control values. In another embodiment, the change in light scattering after step (c) is compared to control values.

A still further method utilizes the direct precipitation of the immunoreactant formed. The amount of binding may also be determined by noting changes in electrophoretic mobility of the liquid admixture of step (c) under non-denaturing conditions.

Yet another method utilizes a receptor of this invention affixed to a soid matrix such as SEPHAROSE beads as an affinity sorbant. Here, the admixture formed in step (b) is a solid/liquid admixture that physically separates the immunoreactant from the liquid portion of the admixture. The liquid portion is thereafter subjected to electrophoretic separation and compared to a similar separation using another aliquot of the sample to determine whether an apolipoprotein A was present in the sample.

It is to be noted that values obtained from appropriate controls are stated as being utilized in several of the methods. It is to be understood that such control values are obtained separately, and may be so obtained before, during or after the recited steps.

III. DIAGNOSTIC SYSTEMS

The present invention also contemplates diagnostic systems, preferably in kit form. Several embodiments of a diagnostic system are contemplated. However, each diagnostic system comprises at least one package that contains a known amount of a monoclonal receptor of this invention that immunoreacts with and binds to human apolipoprotein A, but is free from immunoreaction with and binding to apolipoproteins B, C, D and E.

Exemplary packages include glass and plastic such as polyethylene and polypropylene bottles or vials; plastic, plastic-metal foil, and plastic-metal foil-paper envelopes, and the like. The receptor may be packaged in an aqueous liquid form as in ascites or buffer, but preferably, the receptor is supplied in dried form such as that provided by lyophilization.

A known amount of the receptor is provided. That amount is at least enough to carry out one assay. The provided receptor is typically supplied in a form and amount that is designed to be diluted to a prescribed volume with water, saline or a buffer such as phosphate-buffered saline at pH 7.3-7.5.

In another embodiment, the system includes a second package that includes a known amount of an apolipoprotein A with which the receptor immunoreacts and binds to form an immunoreactant. The apolipoprotein A is provided affixed to a solid matrix as a solid support antigen.

Useful solid matrices are as already described. Preferably, however, the solid matrix is the well of a microtiter plate. The microtiter plate forms the package for the well, but may also be separately enclosed in a paper envelope or plastic film to avoid contamination of the wells.

In a further embodiment, the receptor is provided affixed to a solid matrix as a solid support. Exemplary of such a solid support are receptor-affixed latex particles that are dispersed in an aqueous medium as previously described.

Additional packages may also be included in the system. Such packages may contain (i) buffer salts in dry or liquid form, (ii) substrates such as hydrogen peroxide and o-phenylenediamine, (iii) an indicating means-containing reagent such as peroxidase-linked goat anti-mouse antibodies in a liquid or dry form, and the like.

It is also noted that the receptor that is required for a diagnostic system of this invention may be any individual receptor of this invention or may be a mixture that contains the antibody-combining sites (idiotype polypeptide portions) of two or more such receptors.

IV. RESULTS

A. Apoprotein Specificity

Each of the four monoclonal antibodies (designated A-I-4 antibody from 611 AV63C2.1F1 hybridoma; A-I-9 antibody from HA62 HA227A2.7D3 hybridoma; A-I-7 antibody from HA60 HA22GF.5F8 hybridoma; and A-II-1 from HA61 H112F3.1A11 hybridoma) was selected on the basis of its capacity to bind intact HDL. Three were selected by screening for antibodies that reacted with the immobilized immunizing antigen using a solid-phase RIA. The fourth (A-II-1) was selected on the basis of indirect precipitation of soluble $^{125}$I-HDL in a fluid-phase assay. In addition to the immunizing antigen, the antibodies produced by each of the four hybridomas bound to immobilized human HDL in a solid-phase RIA, suggesting that each of these antibodies was specific for one of the apolipoproteins of human HDL.

Antibody specificity was determined by Western blotting of the electrophoretically separated apolipoproteins of human VLDL, LDL, and HDL, as well as isolated apo-A-I and apo-A-II. Antibodies A-I-4, A-I-7, and A-I-9 bound completely to apo-A-I of HDL and isolated apo-A-I. Some of the antibodies identified trace amounts of what appeared to be contaminating apo-A-I in both LDL and isolated apo-A-II; i.e., proteins that were marginally visible in the stained gel.

Figure 1:
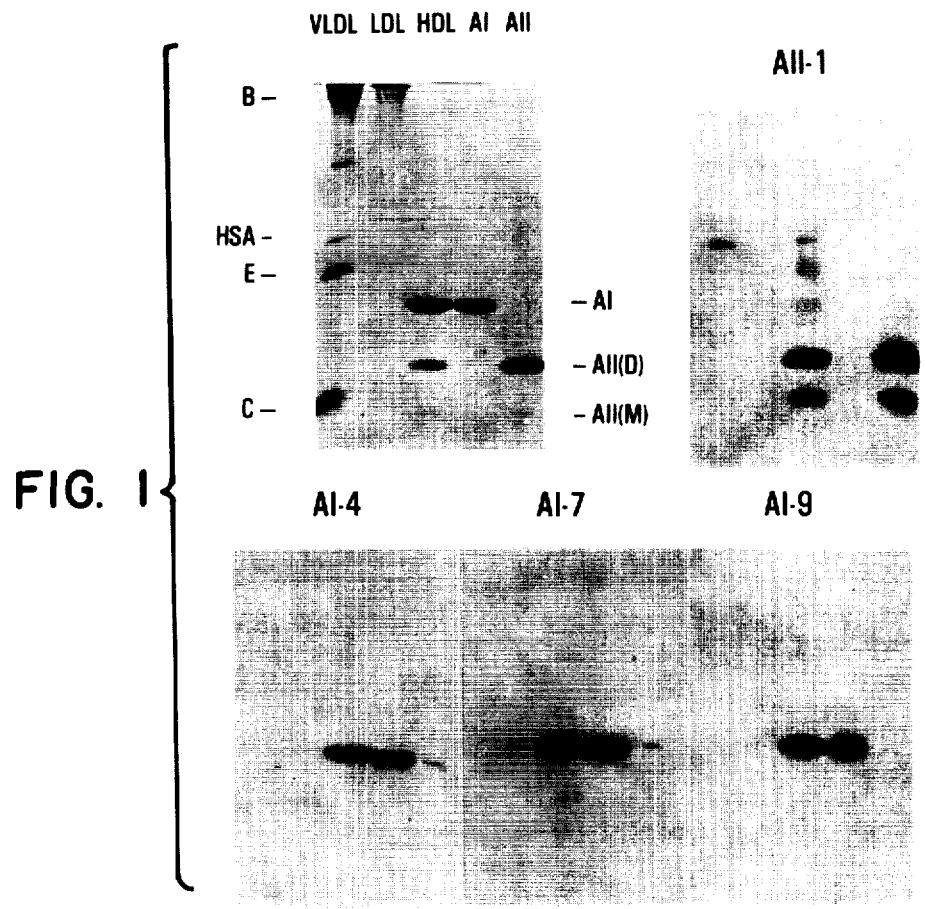
FIG. 1 is a photograph of a polyacrylamide gel electrophoresis (PAGE) separation showing apolipoprotein chain specificity of a mouse monoclonal antibody of this invention for VLDL, LDL, HDL, apo-A-I, and apo-A-II at concentrations of 30, 20, 20, 10, and 10 micrograms, respectively. The samples were electrophoresed in 7.5–20 percent polyacrylamide gradient slab gels containing 0.1 percent sodium dodecyl sulfate (SDS). The top left is a photograph of a Coomassie Brilliant Blue R-250 protein-stained gel before electrophoretic transfer of the apolipoproteins to nitrocellulose. The abbreviations are: B, apo-B; HSA, human serum albumin; E, apo-E; C, apo-C; A-I, apo-A-I; A-II(D), apo-A-II dimers; A-II(M), apo-A-II monomers. The remaining photographs are 24-hour autoradiographs of identical nitrocellulose paper transfers after incubation with the individual hybridoma ascites fluids and $^{125}$I-goat anti-mouse Ig [0.5 micro-Curies/milliliter (micro Ci/ml)]. The antibody numbers above each autoradiograph refer to the apolipoprotein specificity as determined by this procedure. The monoclonal receptors denominated A-II-1, A-I-4, A-I-7, and A-I-9 were used at dilutions of 1:5000, 1:2000, 1:3000, and 1:2000, respectively.

The one exception to this pattern of reactivity was antibody A-II-1. This antibody bound to isolated human apo-A-II dimers and apo-A-II monomers as well as the apo-A-II dimers and monomers of human HDL (FIG. 1).

In addition, this antibody bound a trace VLDL protein of apparent molecular weight of 52,000 daltons that was not readily observed in the protein-stained gel. This protein, which appeared to be present also in HDL, had a mobility that was intermediate between apo-E and albumin, and may have been an apo-E-A-II dimer as described by Weisgraber and Mahley, *J. Biol. Chem.*, 253, 6281–6288 (1978).

Thus, three of the monoclonal antibodies were specific for apo-A-I, and the fourth was specific for apo-A-II. The numerical antibody designations shown in FIG. 1 reflect this apolipoprotein specificity. In addition, each of the apo-A-I antibodies bound multiple apo-A-I isoforms including A-I-1, A-I-2, and pro-A-I from either HDL or isolated apo-A-I, after separation of those isoforms in isoelectric focusing gels.

B. Lipoprotein Specificity

To characterize the reactivity of these antibodies for native HDL, binding of the antibodies to $^{125}$I-HDL was studied in a fluid-phase double-antibody RIA. Antibody binding was measured at a final antigen concentration of 66.7 ng of $^{125}$I-HDL/ml. Maximum binding of $^{125}$I-HDL by each of the four antibodies in antibody excess varied from 18 to 56 percent for the apo-A-I-specific antibodies and was 87 percent for the apo-A-II-specific antibody (FIG. 2). It was notable that 100 percent binding of $^{125}$I-HDL was uniformly expressed by the apolipoprotein chains as organized on all HDL particles.

As reported by Chung and Albers, *J. Lipid Res.* 23, 747–753 (1982), HDL of density equal to 1.063 to 1.21 contains two types of particles: (i) particles that contain apo-A-I and apo-A-II in an approximate 2:1 molar ratio; and (ii) particles that contain apo-A-I but no apo-A-II. Therefore, it was not surprising that the apo-A-II antibody did not bind 100 percent of HDL. However, if all HDL particles contained at least apo-A-I, other explanations must exist for the inability of any one of the three apo-A-I antibodies to bind all HDL. Because each of the antibodies bound all isoforms of the isolated apolipoprotein after electrophoresis in SDS, the ability of these antibodies to recognize the isolated apolipoprotein in a fluid-phase RIA also was examined.

Antibody A-II-1 bound 100 percent of $^{125}$I-apo-A-II (FIG. 2). Therefore, this protein chain appeared to be immunochemically homogeneous in that all apo-A-II molecules expressed the epitope defined by the A-II-1 antibody.

However, none of the apo-A-I-specific antibodies bound 100 percent of soluble $^{125}$I-apo-A-I (FIG. 2). In antibody excess, antibodies A-I-4, A-I-7, and A-I-9 bound 55, 60, and 13 percent of $^{125}$I-apo-A-I, respectively.

To determine if there was a difference in the apolipoprotein composition of $^{125}$I-HDL particles bound by each antibody, as opposed to those particles that were not bound by antibody, precipitates and supernatants formed in the presence of high concentrations of monoclonal antibody (and a slight excess of precipitating antibody to fully precipitate all monoclonal antibody) were dissolved in SDS and electrophoresed on SDS-PAGE. A representative autoradiograph of the bound (precipitate) and unbound (supernatant) fractions of $^{125}$I-HDL after reaction with antibodies A-I-7, A-II-1, and A-I-4 is shown in FIG. 3.

All apo-A-I-specific antibodies, including antibodies A-I-4 and A-I-7, bound $^{125}$I-HDL particles that contained both apo-A-I and apo-A-II, and the bound fractions were indistinguishable from either the starting $^{125}$I-HDL or the unbound $^{125}$I-HDL; i.e., the unbound $^{125}$I-HDL contained nonprecipitable apo-A-I. In contrast, antibody A-II-1 appeared to bind most if not all of the $^{125}$I-HDL that contained apo-A-II, because the unbound supernatant fraction from this reaction mixture was free of demonstrable apo-A-II dimers or monomers (FIG. 3). Thus, antibody A-II-1 bound all HDL particles that contained apo-A-II, whereas none of the A-I-specific antibodies were capable of binding all HDL particles that contained only apo-A-I.

C. Incomplete Binding of Antigen

To explain the inability of the apo-A-I-specific antibodies to bind to and facilitate total precipitation of either $^{125}$I-HDL, soluble $^{125}$I-HDL or soluble $^{125}$I-apo-A-I, two general possibilities were considered: (i) heterogeneity of apo-A-I with respect to expression of epitopes; and (ii) nonoptimal conditions of analysis of binding. In initial studies, the optimum time and temperature was determined for the maximum binding of antibodies A-I-4, A-I-7, A-I-9, and A-II-1 to $^{125}$I-HDL in fluid phase. For each of these antibodies, maximal binding was observed within 18–20 hours at either 4 or 24 degrees C. The quantity of $^{125}$I-HDL that was bound by each antibody was maximal and independent of the amount of antibody added under conditions of antibody excess. In additional studies, it was shown that (a) antibody binding was independent of the amount of antigen added; i.e., antibody affinity; (b) radioiodination of apo-A-I or HDL did not interfere with antibody binding; (c) mild antigen dissociating conditions such as heating and detergents did not expose additional antigen epitopes; and (d) individual allytypic differences in apo-A-I did not account for the incomplete binding of HDL.

Because none of the above manipulations led to complete binding of HDL, the alternative possibility was considered that there may be heterogeneity of apo-A-I. It was hypothesized that all apo-A-I molecules in plasma were not absolutely identical; i.e., all molecules of apo-A-I did not uniformly express the epitopes defined by the three apo-A-I-specific antibodies. If each apo-A-I antibody bound a different epitope on apo-A-I, and if all HDL particles contained an apo-A-I expressing one or more of these epitopes, then complete binding of all $^{125}$I-HDL particles would be observed by combining the three apo-A-I-specific antibodies. When all possible combinations of two or three apo-A-I-specific antibodies were analyzed for binding, only incomplete binding of $^{125}$I-HDL was observed as shown in Table 1, below.

TABLE 1

| All $^{125}$I-HDL Bound By One Apo-A-II-Specific And Three Apo-A-I-Specific Antibodies | | |
|---|---|---|
| | $^{125}$I-HDL bound (% of maximum) | |
| Antibody | Alone | In combination |
| A-I-4, A-I-7 | 44 ± 1; 61 ± 3 | 80 ± 3 |
| A-I-4, A-I-9 | 44; 32 ± 2 | 63 ± 2 |
| A-I-7, A-I-9 | 61; 32 | 76 ± 4 |
| A-I-4, A-I-7, A-I-9 | 44, 61, 32 | 83 ± 3 |
| A-II-1, A-I-4 | 67 ± 6, 44 | 92 ± 2 |
| A-II-1, A-I-7 | 67; 61 | 93 ± 1 |
| A-II-1, A-I-9 | 67; 32 | 87 ± 3 |

TABLE 1-continued

| All $^{125}$I-HDL Bound By One Apo-A-II-Specific And Three Apo-A-I-Specific Antibodies | | |
|---|---|---|
| | $^{125}$I-HDL bound (% of maximum) | |
| Antibody | Alone | In combination |
| A-II-1, A-I-4, A I-7 | 67, 44, 61 | 100 ± 2 |
| A-II-1, A-I-4, A I-9 | 67, 44, 32 | 98 ± 3 |
| A-II-1, A-I-7, A I-9 | 67, 61, 32 | 99 ± 1 |

$^{125}$I-HDL was used at 66.7 ng/ml in the fluid-phase RIA

In view of the before-discussed results, each of the apo-A-I-specific antibodies must bind a different epitope because as each additional antibody was added, additional apolipoprotein A-I was bound, although all antibodies were present in excess. All combinations of the A-I antibodies were present in excess. All combinations of the A-I antibodies bound more HDL than any single A-I antibody, and the oligoclonal mixture of the three apo-A-I antibodies, and the oligoclonal mixture of the three apo-A-I antibodies most closely approached complete binding of $^{125}$I-HDL. These results suggest that HDL particles may exist that either do not contain apo-A-I or contain apo-A-I molecules that are not recognized by any of these apo-A-I-specific antibodies.

Because complete binding of $^{125}$I-HDL could not be obtained with any combination of the three apo-A-I-specific antibodies, binding all $^{125}$I-HDL was examined by combining each of the apo-A-I-specific antibodies individually with the apo-A-II-1 antibody (Table 2).

TABLE 2

| The Percent Of $^{125}$I-HDL Bound By Each Antibody Was Independent Of The Amount Of $^{125}$I-HDL Added | | | |
|---|---|---|---|
| $^{125}$I-HDL Added | $^{125}$I-HDL Bound (Percent of Maximum) | | |
| (ng/ml) | A-I-4 | A-I-7 | A-I-9 |
| 10 | 31.8 ± 2.8 | 43.7 ± 3.1 | 30.2 ± 0.5 |
| 30 | 30.6 ± 4.1 | 42.0 ± 7.7 | 29.0 ± 2.3 |
| 100 | 33.3 ± 1.1 | 44.4 ± 0.6 | 29.2 ± 1.1 |
| 300 | 34.7 ± 3.2 | 44.4 ± 1.7 | 29.1 ± 1.2 |

To insure that each of the apo-A-I-specific antibodies identified all apo-A-I isoforms, HDL and isolated apo-A-I were separated by isoelectric focusing in polyacrylamide gels and were Western blotted to nitrocellulose for reaction with antibody. The left panel of FIG. 1 is a photograph of a Coomassie Brilliant Blue R250 stained gel before electrophorectic transfer of the apolipoproteins to nitrocellulose. The remaining three panels are 24 hour autoradiographs of identical nitrocellulose paper transfers after incubation with each of the individual antibodies and $^{125}$I-goat-anti mouse Ig (0.5 milliCi/ml). As shown, each apo-A-I antibody bound multiple apo-A-I bands, suggesting that none of the antibodies distinguished among the various isoforms. No combination of one apo-A-I-specific antibody with antibody A-II-1 resulted in 100 percent binding of $^{125}$I-HDL.

However, the combination of any two apo-A-I-antibodies with the single apo-A-II-specific antibody resulted in 100 percent binding of $^{125}$I-HDL (Table 1). Those results confirm that all HDL particles express at least one of the three apolipoprotein epitopes defined by antibodies A-II-1, A-I-4, and A-I-7; A-II-1, A-I-4, and A-I-9; or A-II-1, A-I-7, and A-I-9, and thus establish limits on the degree of heterogeneity.

B. HDL and Apoprotein Affinity

Because complete binding of $^{125}$I-HDL could be achieved with an oligoclonal mixture of monoclonal antibodies, the feasibility of using these antibodies to accurately quantitate total plasma HDL was further analyzed. The quantity of apo-A-I measured in HDL and apo-HDL with polyclonal antisera has often been different, suggesting that the affinities of antibodies might differ for soluble apolipoproteins as compared with the same apolipoproteins when they are organized on HDL. Competitive RIAs with $^{125}$I-HDL were used in which the ability of HDL and the isolated apolipoprotein to compete for binding of $^{125}$I-HDL was analyzed to identify differences in antibody affinities for HDL and apo-HDL.

Slope analysis of the logit-transformed competitive curves indicated that two of the antibodies, A-I-7 and A-II-1, had the same affinity for the isolated apolipoprotein and for that apolipoprotein when organized on HDL, whereas the other two antibodies, A-I-4 and A-I-9 differed. For both antibodies A-I-4 and A-I-9, the affinities were less for free apo-A-I than for apo-A-I organized on HDL.

C. Expression of Apo-A-I and Apo-A-II Epitopes by Apoproteins of Different Biosynthetic Origin The apo-A-I and apo-A-II epitopes defined by the antibodies of this invention were examined to determine if apolipoproteins from different biosynthetic sites differed in epitope expression. Included in this analysis were (a) conditioned culture medium from the hepatic cell line Hep G2; (b) human lymph collected by thoracic duct drainage; and (c) unfractionated whole plasma, lipoprotein-depleted plasma, VLDL, and HDL from the same pooled plasma source. Each of those samples was examined for epitope expression by competitive inhibition immunoassay for each monoclonal antibody using $^{125}$I-HDL as the ligand. Inhibition was based on total protein added. The $^{125}$I-HDL used in each immunoassay was obtained from a pooled plasma source.

Each apolipoprotein source was analyzed at three levels. First it was determined whether the protein competitvely inhibited antibody binding to $^{125}$I-HDL. Second, if inhibition was observed, the affinity of the antibody for the competing protein was determined by slope analysis and compared with the affinity for HDL. Third, if similar affinities were observed, the quantitative expression of the epitope by the competing protein (based on total protein added) was compared with that expressed by either HDL or plasma. If the affinities were not the same as determined by slope analysis, no quantitative conclusions could be drawn.

The epitope defined by antibody A-I-4, which bound a subset of apo-A-I present on 40-50 percent of $^{125}$I-HDL, was not expressed by apo-A-I of VLDL or by hepatocyte-derived apo-A-I present in culture medium from the Hep G2 cells. This epitope was expressed in lipoprotein-deficient plasma (LPDP), but the affinity for the epitope in LPDP was less than the epitope expressed by apo-A-I organized on HDL. As demonstrated previously, the affinity of this antibody for isolated Apo-A-I was less than its affinity for HDL, indicating differences in the defined epitope. This suggested that the majority of the apo-A-I in LPDP was not associated with lipoprotein particles.

In contrast this epitope was expressed by apo-A-I in normal human plasma (NHP) and in thoracic duct lymph (lymph) with an affinity that was indistinguishable from that for plasma-derived HDL, suggesting that the apo-A-I of NHP and lymph was associated with lipid. On the basis of total protein added, more A-I-4 epitope was detected in lymph than in NHP.

Antibody A-I-7, which identified a major apo-A-I epitope denominated A-I-7, also did not bind apo-A-I of plasma VLDL. The A-I-7 epitope expressed by molecules in the Hep G2 culture medium and lymph interacted with a higher affinity compared with HDL, whereas the A-I-7 epitope expressed by molecules in LPDP and NHP interacted with its antibody with an affinity that was indistinguishable from that of the same epitope expressed on HDL.

As demonstrated above, the affinity of this antibody for isolated apo-A-I and apo-A-I in HDL is the same. Thus, this antibody did not appear to distinguish between free or lipid-associated apo-A-I. The difference in affinity of the antibody for the A-I-7 epitope in lymph and hepatocyte medium indicated a modification of apo-A-I in these sources. On a quantitative basis, the amount of apo-A-I in LPDP by reference to the A-I-7 epitope was 11 percent of the apo-A-I present in normal human plasma.

The third apo-A-I epitope identified by antibody A-I-9 was distinguished from epitope bound by antibodies A-I-4 and A-I-7 by its expression by apo-A-I on VLDL, although it was not expressed by molecules in LPDP. The A-I-9 epitope was expressed by apo-A-I from Hep G2 cells in culture.

Compared with HDL, the A-I-9 epitope of apo-A-I of lymph had higher affinity for antibody, that of VLDL had lower affinity, and the same affinity was observed for Hep G2 culture medium and NHP. The epitope bound by antibody A-I-9 was thus subject to fine differences in structure on different apo-A-I.

The apo-A-II epitope identified by antibody A-II-1 was present in all samples studied. Compared with HDL, the A-II-1 epitope was expressed with the same affinity by molecules in Hep G2 culture medium, LPDP, and NHP. This apo-A-II epitope interacted with epitopes that appeared the same for isolated apo-A-II and apo-A-II organized in HDL. The apo-A-II of LPDP represented 3.4 percent of the apo-A-II present in NHP. Surprisingly, the binding affinity of this antibody for apo-A-II in VLDL and lymph was slightly greater than its affinity for HDL.

D. Expression of Apo-A-I and Apo-A-II Epitopes in HDL Subfractions

Figure 4:
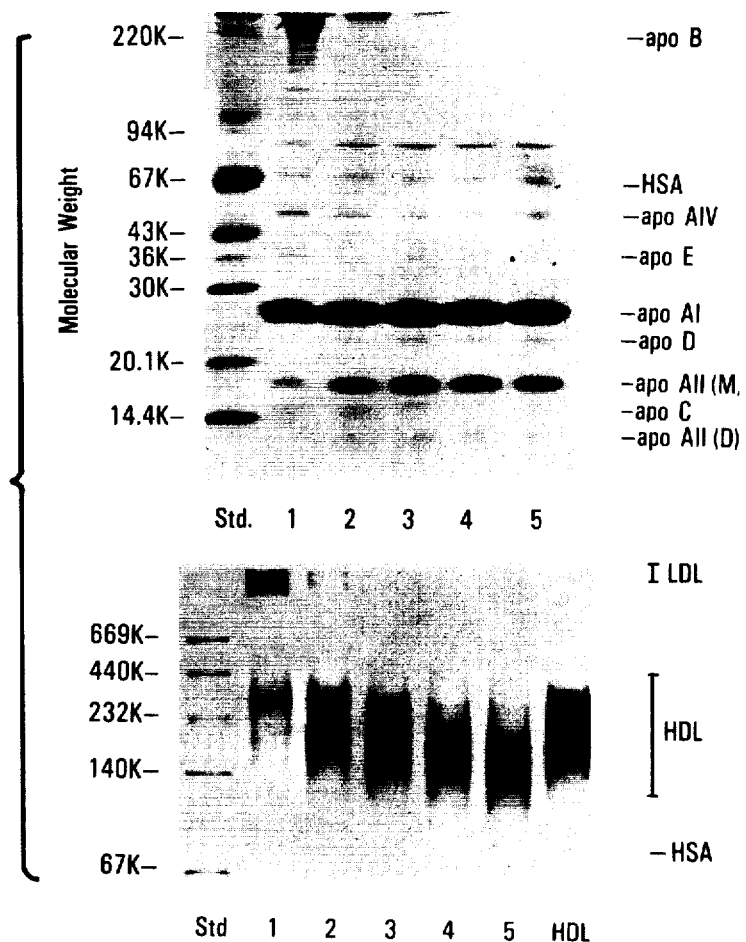
FIG. 4 is a photograph of a 24-hour radioimmunoassay following polyacrylamide gel electrophoresis of the five HDL subfractions isolated by density gradient ultracentrigugation in KBr. A fraction of plasma brought to a density of 1.063 grams per milliliter (g/ml) with KBr was centrifuged for 48 hours at 10 degrees C. in a Beckman 60 Ti ultracentrifuge rotor at 54,000 rpm. The gradient was fractionated from the top, and the 4.0-ml fractions were dialyzed into 0.15 molar (M) NaCl containing 0.1 percent ethylenediaminetetracetic acid (EDTA). The upper photograph shows the protein-staining pattern of the fractions after electrophoresis on a 7.5–20 percent acrylamide gradient gel in the presence of 0.1 percent SDS to visualize the apolipoproteins. The bottom photograph shows the protein-staining pattern of the same density fractions after electrophoresis on a 4–30 percent acrylamide gradient gel in the absence of a denaturant for separation of intact lipoprotein particles on the basis of size. The total cholesterol of HDL fractions 1 through 5 was 498, 321, 231, 194, and 222 micrograms per milligram (ug/mg) protein, respectively.

Epitope expression by HDL subpopulations separated by density gradient ultracentrifugation and chromatofocusing was examined to determine if HDL subpopulations differing in apo-A-I and apo-A-II epitopes could be distinguished on the basis of particle size or composition. Five HDL density subfractions were isolated from a single plasma source that was pooled from three donors. The apoprotein composition of the subfractions was characterized by SDS-PAGE (sodium dodecyl sulfate-polyacrylamide gel electrophoresis), and the particle size distribution of particles present in these HDL subfractions was characterized by PAGE (FIG. 4).

HDL density subfraction 1 (the lowest density HDL) was distinguished by SDS-PAGE from fractions 2 through 5 by the presence of apo-B, greater quantities of apo-E, and relatively small amounts of apo-A-II (dimer and monomer) and apo-D. Because these HDL subfractions were obtained from a single ultracentrifugation to minimize apoprotein loss and potential perturbation of the HDL particles, they also contained small amounts of other plasma proteins (FIG. 4, top).

Electrophoresis of the HDL density subfractions on 4–30 percent polyacrylamide gradient (PAGE) pore gels in the absence of SDS or other dissociating agents demonstrated the presence of varying proportions of HDL particles of at least two sizes. Predominantly large HDL particles were present in density subfractions 1 and 2, and small HDL particles predominated in subfractions 4 and 5 (FIG. 4, bottom). In addition, the HDL subfractions differed with respect to their total cholesterol content. The light HDL fractions (1 and 2) contained the largest amount of free and esterified cholesterol/mg of total protein.

When epitope expression by each HDL subfraction was analyzed by competitive inhibition, complete inhibition of the binding of each antibody could be achieved, confirming that each of the defined epitopes was present in each HDL fraction. When the competitive inhibition profiles were analyzed by logit transformation to compare the qualitative epitope expression by each subfraction, slope analysis indicated that the affinity of each epotope for its antibody did not significantly differ one from another (p less than or equal to 0.2). Thus, a relative assessment of the quantitative expression of each epitope in each HDL subfraction was feasible.

From the competitive inhibition regression line, the protein required for 50 percent inhibition of antibody binding was determined (Table 3). On a quantitative basis, epitopes A-I-4 and A-I-9 were expressed at highest concentration by subfraction 2, whereas epitope A-I-7 was most highly expressed by subfractions 4 and 5. Epitope A-II-1 was most abundant in subfraction 4 as set forth in Table 3 below.

TABLE 3

| Quantitative Expression Of Apolipoprotein A-I And A-II Epitopes And HDL Subfractions | | | | |
|---|---|---|---|---|
| | Competitor concentration per antibody[a] | | | |
| | A-I-4 | A-I-7 | A-I-9 | A-II-1 |
| HDL density fractions[b] | | | | |
| 1 (light) | 137 | 20.5 | 19.5 | 1.08 |
| 2 | 46 | 9.5 | 8.4 | 0.44 |
| 3 | 78 | 7.4 | 14.8 | 0.39 |
| 4 | 78 | 6.4 | 21.9 | 0.32 |
| 5 (heavy) | 84 | 6.4 | 32.0 | 0.49 |
| HDL chromatofocusing fractions[c] | | | | |
| 11 (pH 5.0) | 72 | 3.3 | 5.6 | 2.70 |
| 18 | 59 | 3.0 | 5.4 | 1.75 |
| 27 | 23 | 1.5 | 7.4 | 0.82 |
| 32 | 20 | 1.8 | 8.2 | 0.53 |
| 34 | 23 | 1.6 | 10.3 | 0.40 |
| 37 (pH 4.4) | 109 | 6.0 | 27.0 | 1.38 |

[a]Concentration of competing protein required to exhibit 50 percent inhibition of antibody binding expressed in milligrams of total protein per milliliter.
[b]Fractions were obtained by density gradient ultracentrifugation. Apoprotein compositions and the size distributions are shown in Figure 4. Unfractionated homologous HDL was used as the radiolabeled ligand and was used at a final concentration of 66.7 ng/ml. Mean slopes and minimum correlation coefficients of the logit-transformed inhibition curves by all HDL density subfractions with antibodies A-I-4, A-I-7, A-I-9, and A-II-1 were: $-3.01 \pm 0.30$, r greater than or equal to 0.995; $-2.94 \pm 0.13$, r greater than or equal to 0.996; $-2.27 \pm 0.14$, r greater than or equal to 0.992; and $-3.16 \pm 0.15$, r greater than or equal to 0.997, respectively. Therefore, no differences were observed in the affinity of each antibody for its epitope in each HDL fraction.
[c]Fractions were obtained by column chromatography as described in the Materials and Methods section (V). Unfractionated homologous HDL was used as the radioiodinated ligand and was added at a final concentration of 66.7 ng/ml. Mean slopes and minimum correlation coefficients of the logit-transformed inhibition curves by all HDL chromatofocusing fractions with antibodies A-I-4, A-I-7, A-I-9, and A-II-1 were: $-3.11 \pm 0.24$, r greater than or equal to 0.995; $2.87 \pm 0.21$, r greater than or equal to 0.994; $-2.06 \pm 0.17$, r greater than or equal to 0.997; and $-3.36 \pm 0.13$, r greater than or equal to 0.998, respectively.

Figure 5:
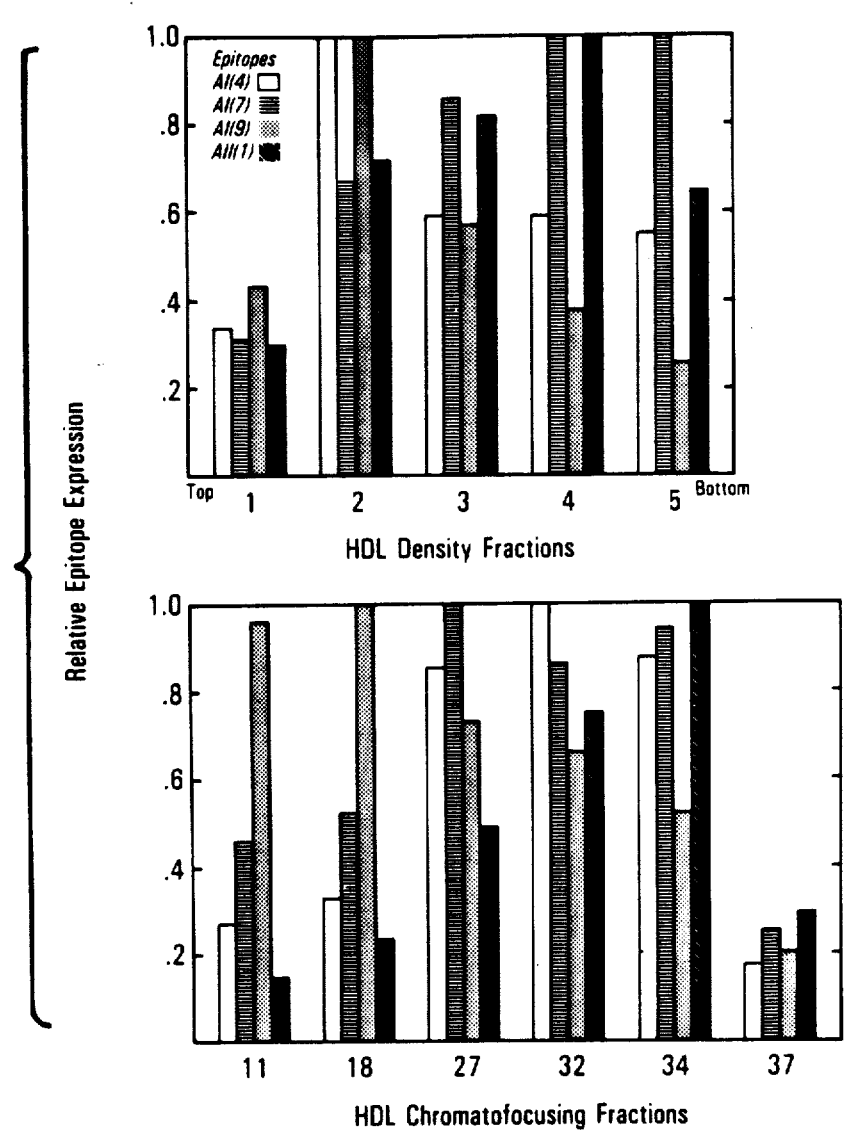
FIG. 5 is a bar graph representing the relative expression of apo-A-I and apo-A-II epitopes in HDL subpopulations. The upper portion shows HDL fractions 1 through 5 obtained by density gradient ultracentrifugation. The lower portion shows HDL fractions from the PBE 94 chromatofocusing column. Data shown were obtained from logit-transformation analysis of the competitive RIAs. The relative epitope expression in each density or chromatofocusing HDL subfraction was obtained by assigning for each antibody a value of 1.0 to the fraction that required the least amount of protein (ug/ml) for 50 percent inhibition of antibody binding. For each antibody, other density or chromatofocusing fractions were then expressed as a fraction of that value.

A comparison of the quantitative expression of the four apoprotein epitopes in the five HDL subfractions is illustrated in FIG. 5 (top). Relative epitope expression for each antibody was calculated from Table 3 by assigning a value of 1.0 to the HDL subfraction that contained, on a protein basis, the greatest quantity of the epitope. All other HDL subfractions were then expressed fractionally. As shown, the relative epitope expression varied for each density subfraction with epitopes A-I-4 and A-I-9 predominating in the light HDL subfractions and epitopes A-I-7 and A-II-1 predominating in the heavy HDL subfractions.

Figure 6:
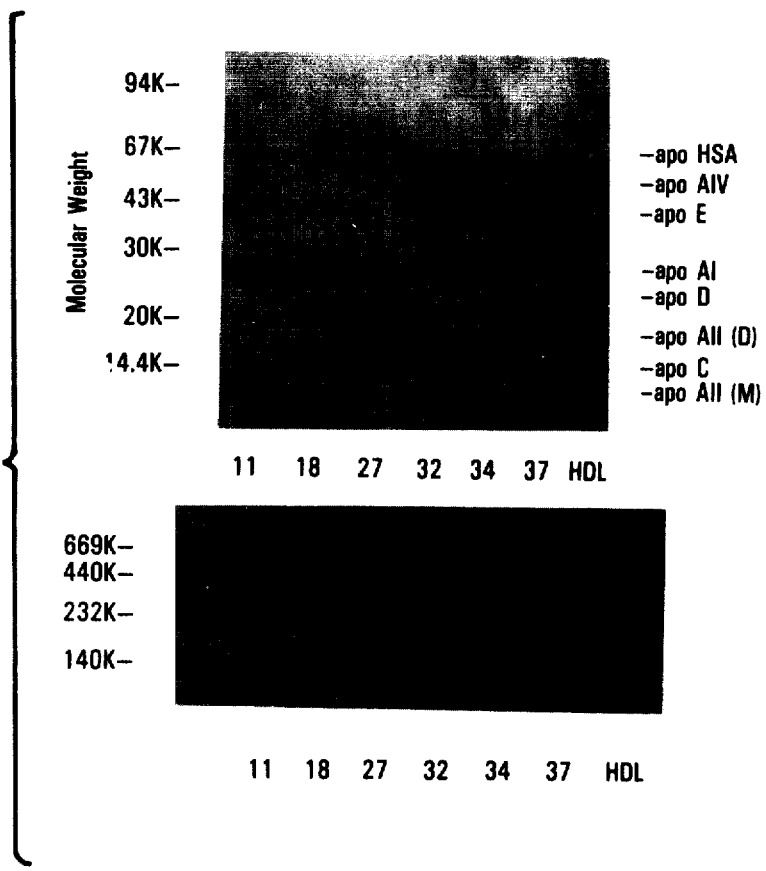
FIG. 6 is a photograph of an autoradiograph of representative HDL chromatofocusing fractions following polyacrylamide gel electrophoresis. A fraction of plasma having a density of 1.063-1.21 g/ml (20 mg protein in 2 ml) was dialyzed into piperazine HCl, having a pH value of 5.8, chromatographed on a PBE 94 column, and eluted with Polybuffer 74. The Polybuffer was removed from selected 4-ml column fractions (11, 18, 27, 32, 34, and 37) by chromatography on Sephadex G-75 with 0.15 M NaCl, 1 millimolar (mM) EDTA, and 0.02 percent NaN$_3$ (having a pH value of 7.4) as eluant. The top photograph is the protein staining pattern after electrophoresis on a 7.5–20 percent acrylamide gradient gel in the presence of 0.1 percent SDS to identify the particle size distribution of each fraction. The bottom photograph is of the same HDL fractions after electrophoresis on a 4–30 percent polyacrylamide gradient pore gel to identify the particle size distribution. Total cholesterol of HDL fractions 11 through 37 above was 294, 233, 183, 174, 190, 185, and 93 micrograms/mg protein, respectively.
Figure 7:
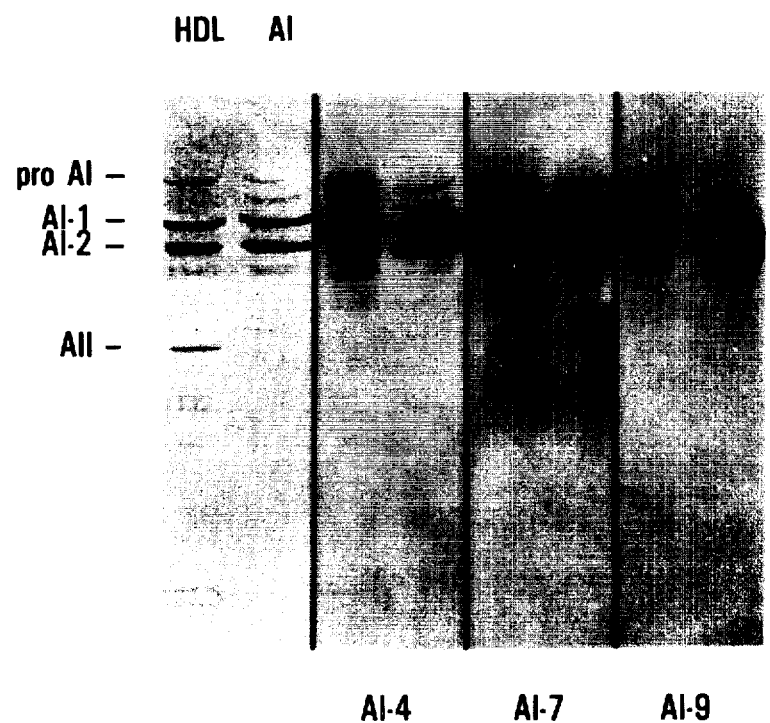
FIG. 7 is a photograph of an autoradiograph of a Western blot analysis performed to delineate apo-A-I isoforms. Increasing amounts of each radiolabeled apolipoprotein or lipoprotein were paired with decreasing amounts of homologous non-radioiodinated antigen so that a constant amount of total antigen was added to each RIA to insure that radioiodination of the ligands did not interfere with antibody binding. Varying proportions of labeled and nonlabeled HDL (FIG. 7A) or soluble apolipoprotein (FIG. 7B) were incubated with each monoclonal antibody for 18 hours at 4 degrees C. Constant concentrations of 133.3 nanograms per milliliter (ng/ml) HDL ($^{125}$I-HDL plus homologous HDL), and 33.3 ng/ml apo-A-I or apo-A-II ($^{125}$I-apo-A-I plus homologous apo-A-I, or $^{125}$I-apo-A-II plus homologous apo-A-II) were maintained.

This same epitope analysis was performed on another set of HDL subfractions separated on the basis of net charge by chromatofocusing. A single plasma source pooled from three donors was used to isolate a d=1.063–1.21 g/ml HDL fraction by ultracentrifugation that was then chromatographed on a Polybuffer-Exchange 94 column. The apoprotein composition of representative subfractions as determined by SDS-PAGE, and the particle size distribution of the same subfractions as determined by PAGE are illustrated in FIG. 6. Fractions 11 and 18 were distinguished from subfractions 32 and 34 by the smaller quantity of apo-A-II (FIG. 6, top). PAGE demonstrated the presence of varying proportions of at least two particle sizes. Subfractions 11 and 18 contained predominantly large cholesterol-rich HDL, whereas subfractions 34 and 37 contained predominately small cholesterol-poor HDL (FIG. 6, bottom).

When epitope analysis was performed, complete competitive inhibition of the binding of each antibody was observed in excess antigen. The affinity of each antibody for its complementary epitope expressed by particles in each chromatofocusing subfraction was equivalent (p equals 0.2). From the competitive inhibition regression lines, the total protein required for 50 percent inhibition was determined (Table 3). On a quantitative basis, epitope A-I-9 was most abundant in subfractions 11 and 18, epitopes A-I-4 and A-I-7 were most abundant in fractions 27, 32, and 34, whereas epitope A-II-1 was present in fraction 34 (FIG. 6, bottom). The most striking feature of the distribution of each of the apoprotein epitopes was the predominance of epitope A-I-9 in HDL particles eluted at pH 5.0 that appeared to contain only apo-A-I (FIG. 6).

V. MATERIALS AND METHODS

A. Lipoproteins

During the course of these studies, lipoproteins were isolated from nine different plasma pools, each made up of three or more individual fasting donors. The isolated lipoproteins, including LDL, density equal to 1.006 g/ml; LDL, density equal to 1.019 to 1.063 g/ml; and HDL density equal to 1.063 to 1.21 g/ml, were dialyzed against lipoprotein buffer (LLB) containing 150 mM NaCl, 1 mM EDTA, 0.005 percent alpha-tocopherol, and 5 mM benzamidine, and were stored under sterile conditions for no more than 21 days. In selected studies to identify potential allelic differences, the HDL (density equal to 1.063 to 1.21 g/ml) was isolated from plasmas obtained from individual normolipidemic donors and treated in the same manner.

HDL density subfractions were obtained from a single pooled plasma source by isopycnic density gradient ultracentrifugation. After removal of the lipoprotein of density less than or equal to 1.063 g/ml by a single 18-hour run at 200,000xg, the infranatant plasma fraction (20 ml) was increased to a density of 1.21 g/ml and centrifuged at 10 degrees C through 20 ml of 1.21 g/ml KBr for about 4 to about 8 hours at 200,000xg. Five 4-ml fractions were collected beginning at the top of the tube, and were dialyzed into LLB for further analysis.

HDL chromatofocusing fractions were obtained from a separate pooled plasma source essentially as described by Nestrock et al., *Biochem. Biophys. Act*, 753, 65–73 (1983). The HDL (density equal to 1.063 to 1.21 g/ml) was isolated by ultracentrifugation and dialyzed into 25 mM piperazine hydrochloride, having a pH value of 5.8. Forty mg of protein were applied to a 1.6×30 cm column of Polybuffer-Exchanger 94 (Pharmacia Fine Chemicals, Piscataway, N.J.; hereinafter Pharmacia) equilibrated with 25 mM piperazine HCl, pH 5.8, and the HDL was eluted with Polybuffer 74 (Pharmacia) diluted 1:15 with $H_2O$, having a pH value of 4.0. The effluent was monitored for absorbance at 280 nanometers (nm) and for pH value. Six HDL subpopulations corresponding to those described by Nestrock et al., (supra), and eluting at pH maximal values of 5.0, 4.9, 4.8, 4.7, 4.5, and 4.4, respectively, were collected and desalted by chromatography on Sephadex G-75 equilibrated with LLB.

B. Isolation of Apoproteins A-I and A-II

Apoproteins A-I and A-II were isolated from ether-/ethanol-delipidated HDL by chromatography on DEAE-cellulose in deionized 6 M urea as described below and by Blaton et al., *Biochemistry*; 16, 2157–2163 (1977). The isolated apolipoproteins were stored in dilute solution in 0.1 percent sodium bicarbonate at −20 degrees C.

C. Lipoprotein Characterization

Lipoproteins were analyzed for protein by a modification of the method of Lowry [Lowry et al., J. Biol. Chem. 193, 265–275 (1951)]in the presence of SDS using a bovine albumin standard. Lipoprotein concentrations were expressed as the mass of protein. Total and free cholesterol were measured by the enzymatic fluorometric method. Esterified cholesterol was taken as the difference between total and free cholesterol. Results were expressed as micrograms of cholesterol/mg of total protein.

The apolipoprotein composition of the lipoproteins was analyzed by polyacrylamide slab gel electrophoresis in the presence of 0.1 percent SDS as described by Curtiss et al., *J. Biol. Chem.*, 257, 15213–15221 (1982). The running gels contained a linear 7.5–20 percent acrylamide gradient. The apo-A-I isoforms were separated by isoelectric focusing in a 6 percent polyacrylamide gel containing 8 M urea and 2 percent Ampholine (1 percent having a pH value between 4–6 and 1 percent having a pH value between 5–8) as described by Weisgraber et al., *J. Lipid Research*, 21, 316–325 (1980). Lipoproteins were delipidated by boiling for 3 minutes in 1 percent SDS before electrophoresis, and the gels were stained after electrophoresis with 0.1 percent Coomassie Brilliant Blue R-250 in 50 percent trichloracetic acid. Gels containing radioiodinated lipoproteins were visualized by autoradiography.

Lipoprotein particle size distributions were determined by lipoprotein polyacrylamide gradient pore gel electrophoresis using the system of [Blanche et al. (*Biochem. Biophys-Acta*, 665; 408–419 (1981))]. Samples containing 10–20 micrograms of protein in 0.008–0.010 ml aliquots were electrophoresed for 24 hours at 130 volts (constant voltage) in 4–30 percent acrylamide gradient slab gels. The high molecular weight calibration kit (Pharmacia) was used for molecular weight determinations. The gels were fixed, stained and destained, and where appropriate, visualized by autoradiography.

D. Generation of Monoclonal Antibodies

The four monoclonal antibodies were obtained from three separate fusions of splenocytes from immunized Balb/c mice (Scripps Clinic and Research Foundation Vivarium, La Jolla, Calif.), using standard fusion protocols discussed herein. Culture supernatants were collected and screened by either solid-phase or fluid-phase radioimmunoassay as described below. All hybridomas were cloned at least twice by limiting dilution, and were stored frozen in liquid nitrogen.

Briefly, Balb/c mice were immunized intraperitoneally with native human HDL or apo-VLDL as immunogen in complete Freund's adjuvant. A booster injection of immunogen in incomplete Freund's adjuvant was administered approximately 3 to 4 weeks following the first injection. Three days prior to harvesting of the mouse spleen, a final booster of immunogen in normal saline was injected intravenously.

The animals so treated were sacrificed, and the spleen of each mouse was harvested. A spleen cell suspension was then prepared. Spleen cells were then extracted from the spleen cell suspension by centrifugation for about 10 minutes at 1000 r.p.m., at 23 degrees C. Following removal of supernatant, the cell pellet was resuspended in 5 ml. cold NH$_4$Cl lysing buffer, and was incubated for about 10 minutes.

To the lysed cell suspension were added 10 ml Dulbecco's Modified Eagle Medium (DMEM) (Gibco) and HEPES [4-(2-hydroxyethyl)-1-piperidineethanesulfonic acid]buffer, and that admixture was centrifuged for about 10 minutes at 1000 r.p.m. at 23 degrees C.

The supernatant was decanted, the pellet resuspended in 15 ml of DMEM and HEPES, and was centrifuged for about 10 minutes at 1000 r.p.m. at 23 degrees C. The immediately preceding procedure was repeated.

The pellet was then resuspended in 5 ml DMEM and HEPES. An aliquot of the spleen cell suspension was then removed for counting.

Fusions were accomplished in the following manner using mouse myeloma cell line P3×63Ag8 for ATCC HB 8744 and line P3×63Ag8.653 for the remaining hybridomas. Using a myeloma to spleen cell ratio of about 1 to 10 or about 1 to 5 (the most preferred myeloma to spleen cell ratio being 1 to 5), a sufficient quantity of myeloma cells were centrifuged to a pellet, washed once in 15 ml DMEM and HEPES, and centrifuged for 10 minutes at 1000 r.p.m. at 23 degrees C. Spleen cells and myeloma cells were combined in round bottom 15 ml tubes (Falcon). The cell mixture was centrifuged for 7 minutes at 800 r.p.m. at 23 degrees C., and the supernatant was removed by aspiration. The remaining cell pellet was then gently broken into large chunks. Thereafter, 200 microliters of 30 percent aqueous polyethylene glycol (w/v) (PEG) (ATCC Baltimore, Md.) at about 16 degrees C. were added, and the mixture was gently mixed for between 15 and 30 seconds. The cell mixture was centrifuged 4 minutes at 600 r.p.m. At about 8 minutes from the time of adding the PEG, the supernatant was removed.

Then 5 ml DMEM plus HEPES buffer was added to the pellet, allowed to set for 5 minutes, and was followed by gently breaking the pellet into large chunks. This mixture was centrifuged 7 minutes at 600 r.p.m. The supernatant was decanted, 5 ml of HT (hypothanthine/thymidine) media were added to the pellet and left undisturbed for 5 minutes. The pellet was then broken into large chunks and the final cell suspension was placed into T75 flasks (2.5 ml per flask) into which 7.5 ml HT media had been placed previously. The resulting cell suspension was incubated at 37 degrees C. to grow the fused cells. Three days after fusion the fused cells were plated out and treated as described below.

In an alternate procedure, the spleens of the two mice were removed, suspended in complete HT medium containing 0.1 millimolar azaguanine [formulated according to Kennett et al., Curr. Top. Microbiol. Immunol., 81, 77 (1978)], pooled to yield $3.2 \times 10^8$ total cells, and fused with mouse myeloma cells in the presence of a fusion promoter [e.g., 30 percent (weight per volume) polyethylene glycol-1000 to about 4000; ATCC]at a ratio of 10 myeloma cells per spleen cell as described in Curtiss et al., J. Biol. Chem., 257, 15213–15221 (1982).

Three days after fusion, viable cells were plated out in 96-well tissue culture plates at $2 \times 10^4$ viable cells per well (768 total wells) in HAT (hypothanthine, aminopterin, thymidine) buffer medium as described in Kennett et al., supra). The cells were fed seven days after fusion with HT medium and at approximately 4–5 day intervals thereafter as needed. Growth was followed microscopically and culture supernatants that contained antibodies were collected on day 14 for assay of antigen-specific antibody production by solid phase radioimmunoassay (RIA).

The hybridomas so prepared were screened, assayed, and their viabilities were determined.

The hybridomas were given the following designations for reference purposes and were deposited on Mar. 5, 1985 with the American Type Culture Collection, Rockville, Md. under the following ATCC of accession numbers.

| Hybridoma | ATCC Accession No. |
|---|---|
| HA62 HA227A2.7D3 | HB 8741 |
| HA61 H112F3.1A11 | HB 8743 |
| HA60 HA22GF.5F8 | HB 8745 |
| 611 AV63C2.111 | HB 8744 |

Immunoglubolin heavy and light chains of the antibodies secreted by the cloned hybridomas were typed using the Mono AB-ID EIA Kit A (Zymed Labs Inc., San Francisco, Calif.). The assays were performed with hybridoma culture supernatants as described by the manufacturer. Those results were as shown below.

| ATCC Accession No. | Isotype |
|---|---|
| HB 8741 | IgG$_1$ kappa |
| HB 8743 | IgM kappa |
| HB 8745 | IgG$_1$ kappa |
| HB 8744 | IgG$_1$ kappa |

E. Monoclonal Antibody Production

Once the desired hybridoma had been selected and cloned, the resultant monoclonal antibody (receptor) was produced in one of two ways. The more pure monoclonal antibody is produced by in vitro culturing of the desired hybridoma in a suitable medium for a suitable length of time, followed by recovery of the desired antibody from the supernatant. Suitable media and length of culturing time are well known in the art, and may be readily determined. The in vitro technique produces essentially monospecific monoclonal antibodies that are substantially free from other specific antibodies. There is often a small amount of other antibodies present since usual media contain exogenous serum (e.g., fetal calf serum). However, this in vitro method may not produce a sufficient quantity or concentration of antibody for some purposes.

To produce a much greater concentration of slightly less pure monoclonal antibody, the desired hybridoma may be injected into mice, preferably syngenic or semi-syngenic mice as described hereinbelow. The hybridoma causes formation of antibody-producing tumors after a suitable incubation time, which result in a relatively high concentration of the desired antibody in the bloodstream and peritoneal exudate (ascites) of the host mouse. Although these host mice also have normal antibodies in their blood and ascites, the concentration of these normal antibodies is typically only about 5 percent of the monoclonal antibody concentration.

Ascites fluids containing the antibodies were obtained from 10-week-old Balb/c mice (Scripps Clinic and Research Foundation), which had been primed with 0.3 ml of mineral oil and injected intraperitoneally with $3-50 \times 10^5$ hybridoma cells.

Alternatively, antibodies were produced by injecting Balb/c mice intraperitoneally with 0.3 ml Pristane (2,6,10,14 tetramethylpentadecane) (Sigma Chemical Co., St. Louis Mo.; hereinafter Sigma). Seven to ten days later, $1-5 \times 10^6$ hybridoma cells in log phase growth were injected intraperitoneally into the same mice. Following a 7-14 day incubation period, ascites fluid was removed from the mice. The concentration of antibody in the ascites fluid was within the range of about 1 to about 10 mg/ml.

F. A-I Vesicle Formation

Lipid-protein complexes were prepared from cholesterol. The lipid-protein complexes were formed into vesicles, purified by Bio Gel P-4 chromatography. Large particles or vesicles were collected for the radioimmunoassay setforth hereinbelow.

The reagents for this procedure were prepared in accordance with the method set forth by Selinger and Lapidot, *J. Lipid Res.*, 7, 174 (1966). Vesicle formation, the formation of a liquid protein complex, was performed in accordance with the method of Pownall et al., *Biochem. Biophys. Acta*, 713, 494-503 (1982). The lipid protein complex was utilized in the isolation of various densities of liquid proteins including VLDL, density of less than 1.006 g/ml; LDL, density equal to 1.019 to 1.063 g/ml; and HDL, density equal to 1.063 to 1.21 g/ml.

G. Enzymatic Cholesterol Assay

The enzymatic cholesterol assay was used to obtain a standard against which the efficacy of the assay was tested. A free cholesterol standard was prepared by serial dilution utilizing cholesterol (U.S.P.) at original concentration of 1 mg/ml, and diluted in 95 percent ethanol to give a final 6 standard points ranging from 1000 ng/15 mCi to 31.25 ng/mCi.

A cholesteryl oleate standard was prepared in the same manner as the free cholesterol standard (Gibco).

Assay solutions were prepared, and the assay of the plasma samples obtained was performed against the above standards utilizing a fluorometer at 325 nanometers, in accordance with the method set forth by Gamble et al., *J. Lipid Res.*, 19,1068-1070 (1978) and Heider and Boyett, *J. Lipid Res.*, 19, 514-581 (1978).

H. Chromatofocusing

Chromatofocusing was performed as a technique to separate HDL from the admixture of lipoproteins found in the plasma pool analyzed in accordance with the method of this invention. Chromatofocusing was performed in accordance with the following method.

The HDL was isolated by ultracentrifugation and dialyzed into 25 mM piperazine hydrochloride having a pH value of 5.8. Forty milligrams of protein was applied to a 1.6 by 30 centimeter column of Polybuffer exchanger 94 (Pharmacia), equilibrated with 25 mM piperazine HCl having a pH value of 5.8, and the HDL was eluted with Polybuffer 74 (Pharmacia) diluted 1 to 15 with an aqueous solution having a pH value of 4.0. Six HDL subpopulations corresponding to those described by Nestrock et al., *Biochem. Biophys. Acta*, 753, 65-73 (1980) in eluting a pH maxima value of 5.0, 4.9, 4.8, 4.7, 4.5, and 4.4, respectively were collected and desalted by chromatography on Sephadex G-75 (Pharmacia) that had been equilibrated with LLB.

I. Iodination of Immunoaffinity Purified Goat Anti-Mouse Immunoqlobulin

Iodination was performed utilizing the Enzymobead iodination procedure and Enzymobeads obtained from Biorad, (Burlingame, Calif.). The Enzymobead iodination was utilized to characterize the antigens and antibodies for the solid phase radioimmunoassay as discussed later herein.

The solid phase radioimmunoassay was performed utilizing a quantitative aliquot of dilute antibodies.

The antibody dilution curve was prepared by the following method. In a series of glass disposable tubes, the following were added in 0.100 ml aliquots: $I^{125}$ antigen plus 9 percent BSA in barbital buffer; competitor in barbital buffer; and first antibody in a 1:40 diluted normal mouse serum or optimum dilution in barbital buffer; 1:40 normal mouse serum in barbital without antibody was added to control tubes. The aliquots were admixed and incubated for four hours at four degrees C.

The tubes were placed on ice and 0.100 ml. of second antibody and barbital buffer, normal goat serum or 100 percent TCA was added. 0.100 Ml of 100 percent trichloroacetic acid were placed in the control tubes in lieu of normal goat serum. The admixture was then incubated on ice for four hours and 2.0 ml of barbital buffer were added at 4 degrees C. The admixtures were then spun for 30 minutes at 2700 r.p.m. (1500 g) at 4 degrees C. The supernatant was aspirated and discarded and counts of the $I^{125}$ gamma emissions were measured. Values for the ratio of bound antibodies to maximum available antibody binding (B/Bo) were calculated as:

$$B/Bo = \frac{(X\ CPM) - (PPT\ CPM)}{(TCA\ CPM) - (PPT\ CPM)}$$

where X is the iodinated sample; PPT is the protein precipitate; TCA is the maximum trichloroacetic acid precipitated radioactivity; and CPM is counts per minute.

J. Solvent Delipidization of Lipoproteins

The lipoprotein to be analyzed was dialyzed against 0.01 percent EDTA having a pH value of 7.5 overnight (approximately 18 hours).

The resulting sample was dialyzed against 0.003 percent EDTA for approximately 12 hours, and was then lyophilized at 10 to 20 milligrams of protein per tube. To each tube was added 35 ml of 1:1 absolute ethanol:anhydrous ether at 4 degrees C. This solution was mixed.

Following mixture, the solution was incubated for 20 minutes at −20 degrees C. The solutions were then spun for 30 minutes at 2000 r.p.m. at 0 degrees C., and the supernatant was poured off.

The ethanol ether extraction as described above was performed twice for a total of three extractions. Then 35 ml anhydrous ether at 4 degrees C. was added to the sample and incubated for 30 minutes at −20 degrees C. The sample was spun at 2000 r.p.m. for 30 minutes at −20 degrees centigrade, and the supernatant poured off and discarded. Pellets were dried using nitrogen gas.

K. Protein Transfers

Proteins were transferred from the polyacrylamide gel (Biorad) using a transfer cassette. Proteins were electrophoresed from the polyacrylamide gel to nitrocellulose (Biorad) . The process employed utilized a 2-hour electrophoreses at 400 milliamperes.

Following the transfer, active sites were blocked utlizing a blocking buffer solution of 24 mM Tris, 192 mM glycine and 20 percent methanol. Incubation of the protein was performed in a two step incubation at 4 degrees C.; one incubation of about 6 hours and the second incubation of about 18 hours.

The proteins were then stained according to manufacturers directions using Coomassie Brilliant Blue-250 (Sigma), destained with 10 percent acetic acid, and dried.

A dilution of antibody was then prepared. Antibody was diluted in blocking buffer (as prepared above). Gel membrane fragments, prepared by the transfer process set forth hereinabove, were then incubated with antibody dilutions for 6 hours at 4 degrees C. The incubated gel membrane fragments were washed in a solution of 0.05 percent Tween-20 [polyoxyethylene (20) sorbitan monolaurate](Sigma), 3.0 percent BSA (Sigma), 3 percent normal goat serum (Sigma) in phosphate buffered-saline for about 30 minutes followed by a LiCl-SDS wash in a solution of 0.5 M LiCl, 0.1 percent SDS in water, for about 10 minutes. This was followed with another wash in the Tween-20 wash solution (as set forth above) for about 30 minutes and blocking with the above blocking buffer additionally containing Tween-20 (Tween Blocking Buffer) for about 18 hours.

Then, a 0.5 micro Ci/ml dilution of $I^{125}$ immuno-purified goat anti-mouse IgG was prepared in Tween-Blocking Buffer. The membranes were incubated in this solution at minimum volume for 4 hours at 4 degrees C. on a horizontal rotator as follows: Tween-20 wash for about 30 minutes; LiCl-SDS wash for 5–10 minutes at 20–22 degrees C.; Tween-20 wash for 30 to 60 minutes; incubation in Tween-Blocking Buffer at minimum volume for about 18 hours and Tween-20 wash for about one hour. Membranes were then air dried on absorbent paper for at least two hours.

L. Radioimmunoassays (RIA)

Solid-phase RIAs were performed in polyvinyl chloride microtiter plates (Falcon, Becton-Dickenson Rutherford, N.J.) as solid supports. The plates were coated with antigen at about 1 microgram per well in 50 microliter aqueous solutions in phosphate-buffered saline (PBS) at pH 7.3. The plates were then maintained for 3 hours at 37 degrees C. The solution was removed, and the wells were washed 3-4 times with PBS. Nonspecific binding sites were then blocked.

The antigen-coated plates were admixed with 50 microliter dilutions of mouse serum, hybridoma culture supernatants or ascites fluids and the admixtures were maintained for about 16–18 hours at 4 degrees C. The solid and liquid admixtures were separated, and the wells were rinsed. Antibody binding was detected by a second admixture following a maintenance period of about 4 hours at 4 degrees C. using 10 ng/well of $^{125}$I-goat anti-mouse Ig (4-4 micro-Ci/microgram as the indicating means.

Fluid-phase RIAs were performed in triplicate in 12×75-mm glass tubes. To 0.1 ml of radioiodinated antigen (human HDL, apo-A-I, or apo-A-II) were admixed 0.1 ml of buffer or competing antigen if present, and 0.1 ml of varying dilutions of mouse hybridoma antibody diluted in 1:60 normal mouse serum. All buffers also contained 5 percent dextran (MW, 40,000). The admixtures were maintained for a time period of 18 hours at 4 or 24 degrees C., at the end of which time 0.1 ml of precipitating second antibody (goat anti-mouse Ig serum) was added. The second antibody was diluted to give a slight antibody excess and complete precipitation of mouse immunoglobulin. That admixture was maintained for a time period of 4 hours, after which time, 2 ml of cold borate buffer was added, and the tubes were centrifuged at 2000×g for 30 minutes. Supernatants were removed by aspiration, and the $^{125}$I content of the pellet was determined in a gamma radiation counter.

Maximum precipitable radioactivity was determined by replacing the goat anti-mouse Ig serum with 100 percent trichloroacetic acid. The minimum precipitable radioactivity or zero binding control (B) was determined by replacing the specific hybridoma antibody with an irrelevant hybridoma antibody of the same heavy chain class.

The minimum precipitable radioactivity or zero binding control (B) was determined by replacing the specific hybridoma antibody with an irrelevant hybridoma antibody of the same heavy chain class.

Data were calculated as either total counts bound or as percent of $^{125}$I-antigen bound =

$$\frac{X - B}{TCA - B} \times 100,$$

where X = mean radioactivity precipitated in the presence of a given amount of specific antibody, and TCA is the maximum trichloroacetic acid-precipitable radioactivity. Competitive radioimmunoassays were analyzed by logit-transformation to compare qualitative and quantitative epitope expression. The variance of the slopes of the competitive inhibitition dose titration regression lines was compared using the Student's t test.

M. Radioiodination

Radioiodination of HDL, apo-A-I, apo-A-II, and immunochemically purified goat anti-mouse Ig was performed enzymatically using immobilized lactoperoxidase and glucose oxidase Enzymobeads, (Biorad). For selected studies, HDL was labeled also with the Bolton-Hunter reagent. The specific activity of $^{125}$I in each preparation of $^{125}$I-HDL was trichloroacetic acid-precipitable, and 5 percent of the radioactivity was extractable into organic solvent. Greater than 99 percent of the radioactivity of $^{125}$I-apo-A-I, $^{125}$I-apo-A-II ranged from 20.9 to 25.5 micro-Ci/microgram.

The preceding description of the invention is set forth by way of example and not of limitation. Others skilled in the art may discern additional applications of the invention that are fully within the scope and spirit of the invention set forth herein.

What is claimed is:

1. A method for assaying for the presence of human apolipoprotein A in a sample to be assayed comprising the steps of:
   (a) providing a monoclonal receptor that is secreted by a hybridoma having an ATCC accession number selected from the group consisting of HB 8741, HB 8743, HB 8744 and HB 8745 and whose antibody combining site immunologically binds to human apolipoprotein A, but does not immunologically bind to human apolipoproteins B, C, D and E;
   (b) admixing a known amount of said receptor with an aliquot of a sample to be assayed for the presence of an human apolipoprotein to form an admixture;
   (c) maintaining said admixture for a predetermined time period sufficient for said receptor to immunologically bind to human apolipoprotein A present in said sample and form an immunoreactant; and
   (d) determining the amount of said receptor bound in said immunoreactant and thereby the presence of said human apolipoprotein A.

2. The method according to claim 1 wherein said receptor is an antibody that immunologically binds to apolipoprotein A-I, and is screted by a hybridoma having an ATCC accession number selected from the group consisting of HB 8741, HB 8744 and HB 8745.

3. The method according to claim 1 wherein said receptor is an antibody that immunologically binds to apolipoprotein A-II, and is secreted by a hybridoma having the ATCC accession number HB 8743.

4. The method according to claim 1 including the additional steps of: (i) providing an apolipoprotein A bound by said receptor that is affixed to a solid matrix as a solid support antigen;
   (ii) admixing the maintained admixture of step (c) present as a liquid admixture with said solid support to form a solid-liquid admixture;
   (iii) maintaining said solid/liquid admixture for a predetermined time period sufficient for said receptor of said liquid admixture to immunologically bind to said antigen and form an immunoreactant;
   (iv) separating said solid and liquid phases; and
   (v) determining the amount of said receptor bound in said immunoreactant.

5. The method according to claim 4 wherein said receptor includes a linked indicating means that signals the formation of said immunoreactant and by which the amount of said receptor bound in said immunoreactant is determined.

6. The method according to claim 1 wherein said sample aliquot is affixed to a solid matrix as a solid support antigen prior to forming the admixture of step (b), the admixture formed is a solid/liquid admixture, and including the further step of separating said solid/liquid admixture prior to determining the amount of bound receptor.

7. The method according to claim 6 wherein the amount of said bound receptor is determined by the steps of:
   (i) admixing a known amount of an indicating means-containing reagent that reacts with the bound receptor of the immunoreactant to form a second solid/liquid phase admixture, said reagent being free from reaction with said solid support antigen, and said indicating means signalling the presence of said bound receptor;
   (ii) maintaining said second admixture for a predetermined time period sufficient for said admixed reagent to react with said bound receptor and form a bound reaction product;
   (iii) separating the solid and liquid phases; and
   (iv) determining the amount of said bound reaction product present.

8. The method according to claim 7 wherein said indicating means-containing reagent is a $^{125}$I-linked antibody that immunologically binds to said receptor.

9. The method according to claim 1 wherein said admixture of step (b) is a liquid admixture and includes a known amount of a radiolabeled apolipoprotein A-containing antigen, and said determination of bound receptors is carried out by the further steps of:
   (i) admixing an excess of an antibody that precipitates said receptors but does not precipitate human apolipoprotein or said admixed radiolabeled antigen, to form a second liquid admixture;
   (ii) maintaining said second liquid admixture for a predetermined period of time sufficient for said admixed antibody to precipitate said receptors, and form a precipitate and a supernatant;
   (iii) separating said precipitate from said supernatant; and
   (iv) measuring the radioactivity present in said precipitate.

10. The method according to claim 1 wherein said receptor is affixed to a solid matrix of latex particles as a solid support prior to said admixture of step (b), said admixture formed is a dispersion of said receptor-affixed latex particles in an aqueous medium, the formation of said immunoreactant causes said latex particles to agglutinate, and the amount of said receptors bound in said immunoreactant is determined by the time required for said latex agglutination to occur.

11. The method according to claim 1 wherein said receptor is produced by hybridoma ATCC HB 8741.

12. The method according to claim 1 wherein said receptor is produced by hybridoma ATCC HB 8743.

13. The method according to claim 1 wherein said receptor is produced by hybridoma ATCC HB 8744.

14. The method according to claim 1 wherein said receptor is produced by hybridoma ATCC HB 8745.

15. A diagnostic assay system comprising at least one package that contains an effective amount of a monoclonal receptor that is secreted by a hybridoma having an ATCC accession number selected from the group consisting of HB 8741, HB 8743, HB 8744 and HB 8745 and immunologically bind to human apoliproprotein A, but does not immunologically bind to human apolipoproteins B, C, D, and E.

16. The diagnostic system according to claim 15 further including a second package that includes, affixed to a solid matrix as a solid support antigen, a known amount of an apolipoprotein A that is immunologically bound by said receptor.

17. The diagnostic system according to claim 16 wherein said solid support is a well of a microtiter plate.

18. The diagnostic system according to claim 15 wherein said receptor is affixed to a solid matrix as a solid support.

19. The diagnostic system according to claim 18 wherein said solid matrix is a latex particle.

20. A hybridoma having the ATCC accession number HB 8741.

21. A hybridoma having the ATCC accession number HB 8743.

22. A hybridoma having the ATCC accession number HB 8744.

23. A hybridoma having the ATCC accession number HB 8745.

24. A method for assaying the amount of human high density lipoprotein in a sample to be assayed comprising the steps of:
 (a) providing a mixture of monoclonal receptors containing effective amounts of receptors secreted by the hybridoma having the ATCC accession number HB 8743 that immunoreact with apolipoprotein A-II and receptors secreted by any two of the hybridomas having the ATCC accession numbers HB 8741, HB 8744 and HB 8745 that immunoreact with apolipoprotein A-I;
 (b) admixing a known amount of said mixture with a sample to be assayed for the presence of human high density lipoprotein to form an admixture;
 (c) maintaining said admixture for a predetermined period of time sufficient for said receptors to immunoreact with said apolipoproteins A-I and A-II to form immunocomplexes; and
 (d) determining the amount of said receptors bound in said immunocomplexes and thereby the amount of said high density lipoprotein in the sample.

25. The method according to claim 24 wherein said admixing of step (b) is carried out in an aqueous liquid phase.

26. The method according to claim 25 wherein the amount of said receptors bound is determined by the steps of:
 (i) admixing an excess of a labeled antibody that immunoreacts with the bound receptor molecules of the immunocomplexes formed in step (c) and precipitates said immunocomplexes;
 (ii) maintaining the admixture formed in step (c) for a predetermined time period sufficient for said labeled antibody to immunoreact and bind to said bound receptors and precipitate said immunocomplexes containing said bound receptor; and
 (iii) determining the amount of labeled antibody in the precipitate so formed.

27. The method according to claim 24 wherein said admixture formed in step (b) is a solid/liquid phase admixture.

28. A method for assaying for the presence of human apolipoprotein A-II in a sample to be assayed comprising the steps of:
 (a) admixing a sample to be assayed for the presence of human apolipoprotein A-III with an effective amount of a monoclonal receptor secreted by the hybridoma having the ATCC accession number HB 8743 that immunoreacts with human apolipoprotein A-II to form an admixture;
 (b) maintaining said admixture for a predetermined period of time sufficient for said receptor to bind to human apolipoprotein A-II present in said sample and form an immunoreactant; and
 (c) determining the presence of an immunoreactant formed in step (b), and thereby the presence of human apolipoprotein A-II in said sample.

29. A method for assaying for the presence of human apolipoprotein A-I in a sample to be assayed comprising the steps of:
 (a) admixing a sample to be assayed for the presence of human apolipoprotein A-I with an effective amount of a mixture of monoclonal receptors that immunoreact with human apolipoprotein A-I secreted by two of the hybridomas having ATCC accession numbers selected from the group consisting of HB 8741, HB 8744 and HB 8745 to to form an admixture;
 (b) maintaining said admixture for a predetermined period of time sufficient for said receptors to bind to human apolipoprotein A-I in said sample and form an immunoreactant; and
 (c) determining the presence of an immunoreactant formed in step (b), and thereby the presence of human apolipoprotein A-I in said sample.

30. A monoclonal receptor that is secreted by a hybridoma having the ATCC accession number HB 8741 and immunologically binds to human apolipoprotein A-I.

31. A monoclonal receptor that is secreted by a hybridoma having the ATCC accession number HB 8744 and immunologically binds to human apolipoprotein A-I.

32. A monoclonal receptor that is secreted by a hybridoma having the ATCC accession number HB 8745 and immunologically binds to human apolipoprotein A-I.

33. A monoclonal receptor that is secreted by a hybridoma having the ATCC accession number HB 8743 and immunologically binds to human apolipoprotein A-II.

* * * * *

UNITED STATES PATENT AND TRADEMARK OFFICE
CERTIFICATE OF CORRECTION

PATENT NO. : 4,677,057

DATED : June 30, 1987

INVENTOR(S) : LINDA K. CURTISS and THOMAS S. EDGINGTON

It is certified that error appears in the above-identified patent and that said Letters Patent is hereby corrected as shown below:

Column 11, line 43, delete "Y3-Ag12.3" and insert --Y3-Ag1.2.3.--

Column 32, line 47, delete "611 AV63C2.111" and insert --611 AV63C2.1F1--

In Claim 3, line 3, delete "screted" and insert --secreted--

In Claim 28, line 5, delete "A-III" and insert --A-II--

Signed and Sealed this

Twenty-first Day of June, 1988

Attest:

DONALD J. QUIGG

Attesting Officer

Commissioner of Patents and Trademarks